(12) United States Patent
Sigalov

(10) Patent No.: US 11,097,020 B2
(45) Date of Patent: *Aug. 24, 2021

(54) METHODS AND COMPOSITIONS FOR TARGETED DELIVERY

(75) Inventor: Alexander B. Sigalov, Worcester, MA (US)

(73) Assignee: SIGNABLOK, INC., Shrewsbury, MA (US)

( * ) Notice: Subject to any disclaimer, the term of this patent is extended or adjusted under 35 U.S.C. 154(b) by 656 days.

This patent is subject to a terminal disclaimer.

(21) Appl. No.: 13/028,238

(22) Filed: Feb. 16, 2011

(65) Prior Publication Data

US 2011/0256224 A1 Oct. 20, 2011

Related U.S. Application Data

(63) Continuation-in-part of application No. PCT/US2010/052117, filed on Oct. 10, 2010.

(60) Provisional application No. 61/250,465, filed on Oct. 9, 2009.

(51) Int. Cl.
*A61K 51/12* (2006.01)
*A61K 47/69* (2017.01)

(52) U.S. Cl.
CPC ...... *A61K 51/1224* (2013.01); *A61K 47/6917* (2017.08)

(58) Field of Classification Search
None
See application file for complete search history.

(56) References Cited

U.S. PATENT DOCUMENTS

| | | | |
|---|---|---|---|
| 5,059,528 A | 10/1991 | Bollen et al. | |
| 5,128,318 A | 7/1992 | Levine et al. | |
| 5,192,264 A * | 3/1993 | Fossel | A61K 35/14 128/898 |
| 5,652,339 A | 7/1997 | Lerch et al. | |
| 5,676,928 A | 10/1997 | Klaveness et al. | |
| 5,840,688 A | 11/1998 | Tso | |
| 5,965,542 A | 10/1999 | Wasan et al. | |
| 6,004,925 A | 12/1999 | Dasseux et al. | |
| 6,037,323 A | 3/2000 | Dasseux et al. | |
| 6,046,166 A | 4/2000 | Dasseux et al. | |
| 6,139,819 A | 10/2000 | Unger et al. | |
| 6,248,353 B1 | 6/2001 | Singh | |
| 6,306,433 B1 | 10/2001 | Andersson et al. | |
| 6,514,523 B1 | 2/2003 | Sparks | |
| 6,617,134 B1 | 9/2003 | Sirtori et al. | |
| 6,953,840 B2 | 10/2005 | Zhu et al. | |
| 7,288,266 B2 | 10/2007 | Smyth-Templeton et al. | |
| 7,435,717 B2 | 10/2008 | Bisgaler et al. | |
| 7,449,301 B2 | 11/2008 | Matozaki | |
| 7,588,751 B2 | 9/2009 | Ueda et al. | |
| 7,662,410 B2 | 2/2010 | Sligar et al. | |
| 7,740,854 B2 | 6/2010 | Low et al. | |
| 7,824,709 B2 | 11/2010 | Ryan et al. | |
| 2001/0002251 A1 | 5/2001 | Woodburn et al. | |
| 2002/0110604 A1 | 8/2002 | Babish et al. | |
| 2002/0156007 A1 | 10/2002 | Graversen et al. | |
| 2002/0177558 A1 | 11/2002 | Meyerhoff et al. | |
| 2003/0008014 A1 * | 1/2003 | Shelness | 424/499 |
| 2003/0045460 A1 | 3/2003 | Fogelman et al. | |
| 2003/0087819 A1 | 5/2003 | Bielicki | |
| 2003/0171277 A1 | 9/2003 | Fogelman et al. | |
| 2003/0181372 A1 | 9/2003 | Oda et al. | |
| 2004/0067873 A1 | 4/2004 | Dasseux et al. | |
| 2004/0077541 A1 | 4/2004 | Zhu et al. | |
| 2004/0176473 A1 * | 9/2004 | Unger et al. | 514/722 |
| 2004/0229794 A1 | 11/2004 | Ryan et al. | |
| 2004/0254120 A1 | 12/2004 | Fogelman et al. | |
| 2004/0266660 A1 | 12/2004 | Hubsch et al. | |
| 2004/0266671 A1 | 12/2004 | Fogelman et al. | |
| 2005/0239136 A1 | 10/2005 | Hazen et al. | |
| 2005/0281740 A1 | 12/2005 | Gong et al. | |
| 2006/0099148 A1 | 5/2006 | Fisher et al. | |
| 2006/0204566 A1 | 9/2006 | Smyth-Templeton et al. | |
| 2006/0205643 A1 | 9/2006 | Cuzzocrea et al. | |
| 2006/0217312 A1 * | 9/2006 | Dasseux | A61K 9/127 424/520 |
| 2006/0257466 A1 | 11/2006 | Kim et al. | |
| 2007/0065432 A1 | 3/2007 | Xu et al. | |
| 2007/0172653 A1 | 7/2007 | Berkland et al. | |
| 2007/0243136 A1 | 10/2007 | Fisher et al. | |
| 2008/0020400 A1 | 1/2008 | Caulfield | |
| 2008/0286353 A1 | 11/2008 | Gregoriadis | |
| 2009/0004113 A1 | 1/2009 | Wolf | |

(Continued)

FOREIGN PATENT DOCUMENTS

| WO | WO-8702061 A1 * | 4/1987 | ........... A61K 9/1275 |
|---|---|---|---|
| WO | 2001038395 | 5/2001 | |

OTHER PUBLICATIONS

Strittmatter, W.J., et al., "Binding of human apolipoprotein E to synthetic amyloid ,B peptide: Isoform-specific effects and implications for late-onset Alzheimer disease", 1993, PNAS, pp. 8098-8102.*

Kopprasch, S., et al., "The pivotal role of scavenger receptor CD36 and phagocyte-derived oxidants in oxidized low density lipoprotein-induced adhesion to endothelial cells", 2004, Int. J. Biochem. Cell Biol., pp. 460-471.*

Arai, H., et al., "Effect of Ascorbate on Acrolein Modification of Very Low Density Lipoprotein and Uptake of Oxidized Apolipoprotein E by Hepatocytes", 2005, Biosci. Biotech., Biochem., pp. 1760-1762.*

Hazell, L.J., et al., "Oxidation of low-desity lipoprotein with hypochlorite causes transformation of the lipoprotein into a high-uptake form for macrophages", 1993, Biochem J., pp. 165-171.*

(Continued)

*Primary Examiner* — Michael G. Hartley
*Assistant Examiner* — Lance W Rider
(74) *Attorney, Agent, or Firm* — Medlen & Carroll, LLP

(57) ABSTRACT

The disclosure provides compounds and compositions, and methods of using these compounds and compositions, for the targeted delivery of therapeutic agents. In one embodiment, these compositions are used for the tumor-targeted delivery of chemotherapeutic agents useful for treating cancer.

40 Claims, 13 Drawing Sheets

(56) References Cited

U.S. PATENT DOCUMENTS

| | | | |
|---|---|---|---|
| 2009/0012025 A1 | 1/2009 | Hotchkiss et al. | |
| 2009/0068264 A1 | 3/2009 | Richardson et al. | |
| 2009/0110739 A1 | 4/2009 | Lacko et al. | |
| 2009/0311191 A1 | 12/2009 | Annapragada et al. | |
| 2009/0312402 A1 | 12/2009 | Contag et al. | |
| 2010/0311595 A1* | 12/2010 | Ryan | A61K 31/7048 504/359 |
| 2011/0312899 A1* | 12/2011 | Sood | A61K 47/48815 514/19.8 |

OTHER PUBLICATIONS

Shao, B., et al., "Methionine oxidation impairs reverse cholesterol transport by apolipoprotein A-I", PNSA, 2008, p. 12224-12229.*
Maor, I., et al., "Oxidized low density lipoprotein leads to macrophage accumulation of unesterif led cholesterol as a result of lysosomal trapping of the lipoprotein hydrolyzed cholesteryl ester", J. Lipid Res., 1994, pp. 803-819.*
Binger, KJ., et al., "Methionine Oxidation Inhibits Assembly and Promotes Disassembly of Apolipoprotein C-II Amyloid Fibrils", Biochemistry, 2008, pp. 10208-10217.*
Jong, M.C., et al., "Oxidized VLDL Induces Less Triglyceride Accumulation in J774 Macrophages Than Native VLDL Due to an Impaired Extracellular Lipolysis", Anterioscler Thromb Vasc Biol., 2000, pp. 144-151.*
Bergt, C., et al., "The myeloperoxidase product hypochlorous acid oxidizes HDL in the human artery wall and impairs ABCA1-dependent cholesterol transport", PNAS, 2004, p. 13032-13037.*
Gazzaniga, S., et al., "Targeting Tumor-Associated Macrophages and Inhibition of MCP-1 Reduce Angiogenesis and Tumor Growth in a Human Melanoma Xenograft", J. Inv. Derm., 2007, pp. 2031-2041 (Year: 2007).*
Bergt, C., "Reagent or myeloperoxidase-generated hypochlorite affects discrete regions in lipid-free and lipid-associated human apolipoprotein A-I", Biochem. J., pp. 345-354 (Year: 2000).*
Wang, W., et al., "Enhanced Cholesterol Efflux by Tyrosyl Radical-oxidized High Density Lipoprotein is Mediated by Apolipoprotein AI-AII Heterodimers",I JBC, p. 17391-17398 (Year: 1998).*
Elias, E.R., et al., "Clinical Effects of Cholesterol Supplementation in Six Patients With the Smith-Lemli-Opitz Syndrome(SLOS)", Am. J. Med. Genetics, pp. 305-310 (Year: 1997).*
Leek RD, et al. Association of macrophage infiltration with angiogenesis and prognosis in invasive breast carcinoma. Cancer Res 1996; 56:4625-9.
Chellat F, et al. Therapeutic potential of nanoparticulate systems for macrophage targeting. Biomaterials 2005; 26:7260-75.
Oda MN, et al. Reconstituted high density lipoprotein enriched with the polyene antibiotic amphotericin B. J Lipid Res 2006; 47:260-7.
Lacko AG, et al. Prospects and challenges of the development of lipoprotein-based formulations for anti-cancer drugs. Expert Opin Drug Deliv 2007; 4:665-75.
Mooberry LK, et al. Receptor mediated uptake of paclitaxel from a synthetic high density lipoprotein nanocarrier. J Drug Target 2010; 18:53-8.
McConathy WJ, et al. Evaluation of synthetic/reconstituted high-density lipoproteins as delivery vehicles for paclitaxel. Anticancer Drugs 2008; 19:183-8.
Acton S, et al. Identification of scavenger receptor SR-BI as a high density lipoprotein receptor. Science 1996; 271:518-20.
Nissen SE, et al. Effect of recombinant ApoA-I Milano on coronary atherosclerosis in patients with acute coronary syndromes: a randomized controlled trial. Jama 2003; 290:2292-300.
Pitt AR, Spickett CM. Mass spectrometric analysis of HOCl- and free-radical-induced damage to lipids and proteins. Biochem Soc Trans 2008; 36:1077-82.
Shao B, et al. Tyrosine 192 in apolipoprotein A-I is the major site of nitration and chlorination by myeloperoxidase, but only chlorination markedly impairs ABCA1-dependent cholesterol transport. J Biol Chem 2005; 280:5983-93.

Shao B, et al. Myeloperoxidase impairs ABCA1-dependent cholesterol efflux through methionine oxidation and site-specific tyrosine chlorination of apolipoprotein A-I. J Biol Chem 2006; 281:9001-4.
Bergt C, et al. Reagent or myeloperoxidase-generated hypochlorite affects discrete regions in lipid-free and lipid-associated human apolipoprotein A-I. Biochem J 2000; 346 Pt 2:345-54.
Pankhurst G, et al. Characterization of specifically oxidized apolipoproteins in mildly oxidized high density lipoprotein. J Lipid Res 2003; 44:349-55.
Panzenboeck U, et al. Effects of reagent and enzymatically generated hypochlorite on physicochemical and metabolic properties of high density lipoproteins. J Biol Chem 1997; 272:29711-20.
Suc I, et al. Oxidative tyrosylation of high density lipoproteins impairs cholesterol efflux from mouse J774 macrophages: role of scavenger receptors, classes A and B. J Cell Sci 2003; 116:89-99.
Duverger N, et al. Transgenic rabbits expressing human apolipoprotein A-I in the liver. Arterioscler Thromb Vasc Biol 1996; 16:1424-9.
Franceschini G, et al. Apolipoprotein AIMilano. Accelerated binding and dissociation from lipids of a human apolipoprotein variant. J Biol Chem 1985; 260:16321-5.
Daum U, et al. Apolipoprotein A-I (R151C)Paris is defective in activation of lecithin: cholesterol acyltransferase but not in initial lipid binding, formation of reconstituted lipoproteins, or promotion of cholesterol efflux. J Mol Med 1999; 77:614-22.
Shelness GS, Williams DL. Secondary structure analysis of apolipoprotein II mRNA using enzymatic probes and reverse transcriptase. Evaluation of primer extension for high resolution structure mapping of mRNA. J Biol Chem 1985; 260:8637-46.
Sigalov A, et al. Large-scale isolation and purification of human apolipoproteins A-I and A-II. J Chromatogr 1991; 537:464-8.
Chung BH, et al. Preparative and quantitative isolation of plasma lipoproteins: rapid, single discontinuous density gradient ultracentrifugation in a vertical rotor. J Lipid Res 1980; 21:284-91.
Cheung MC, et al. Characterization of high density lipoprotein subspecies: structural studies by single vertical spin ultracentrifugation and immunoaffinity chromatography. J Lipid Res 1987; 28:913-29.
Sigalov AB, Stern LJ. Enzymatic repair of oxidative damage to human apolipoprotein A-I. FEBS Lett 1998; 433:196-200.
Sigalov AB, Stern LJ. Dihydrolipoic acid as an effective cofactor for peptide methionine sulfoxide reductase in enzymatic repair of oxidative damage to both lipid-free and lipid-bound apolipoprotein a-l. Antiox Redox Signal 2002; 4:553-7.
Biewenga GP, et al. Effects of dihydrolipoic acid on peptide methionine sulfoxide reductase. Implications for antioxidant drugs. Arzneimittelforschung 1998; 48:144-8.
Anantharamaiah GM, et al. Effect of oxidation on the properties of apolipoproteins A-I and A-II. J Lipid Res 1988; 29:309-18.
Weiss SJ, et al. Brominating oxidants generated by human eosinophils. Science 1986; 234:200-3.
Lerch PG, et al. Production and characterization of a reconstituted high density lipoprotein for therapeutic applications. Vox Sang 1996; 71:155-64.
Matz CE, Jonas A. Micellar complexes of human apolipoprotein A-I with phosphatidylcholines and cholesterol prepared from cholate-lipid dispersions. J Biol Chem 1982; 257:4535-40.
Toledo JD, et al. Cholesterol flux between lipid vesicles and apolipoprotein AI discs of variable size and composition. Arch Biochem Biophys 2000; 380:63-70.
Sigalov AB, Stern LJ. Oxidation of methionine residues affects the structure and stability of apolipoprotein A-I in reconstituted high density lipoprotein particles. Chem Phys Lipids 2001; 113:133-46.
Jonas A. Reconstitution of high-density lipoproteins. Methods Enzymol 1986; 128:553-82.
Rensen PC, et al. Recombinant lipoproteins: lipoprotein-like lipid particles for drug targeting. Adv Drug Deliv Rev 2001; 47:251-76.
Sigalov AB, et al. The ratio of non-oxidized/oxidized forms of apolipoprotein A-I can affect cholesterol efflux from human skin fibroblasts mediated by high density lipoprotein. Eur J Clin Chem Clin Biochem 1997; 35:395-6.
Kim SI, et al. Targeted delivery of siRNA against hepatitis C virus by apolipoprotein A-I-bound cationic liposomes. J Hepatol 2009; 50:479-88.

(56) References Cited

OTHER PUBLICATIONS

Sorci-Thomas MG, et al. The hydrophobic face orientation of apolipoprotein A-I amphipathic helix domain 143-164 regulates lecithin:cholesterol acyltransferase activation. J Biol Chem 1998; 273:11776-82.

Durbin DM, Jonas A. The effect of apolipoprotein A-II on the structure and function of apolipoprotein A-I in a homogeneous reconstituted high density lipoprotein particle. J Biol Chem 1997; 272:31333-9.

Davidson WS, et al. The effect of high density lipoprotein phospholipid acyl chain composition on the efflux of cellular free cholesterol. J Biol Chem 1995; 270:5882-90.

Chen W, et al. Incorporation of an apoE-derived lipopeptide in high-density lipoprotein MRI contrast agents for enhanced imaging of macrophages in atherosclerosis. Contrast Media Mol Imaging 2008; 3:233-42.

Musanti R, Ghiselli G. Interaction of oxidized HDLs with J774-A1 macrophages causes intracellular accumulation of unesterified cholesterol. Arterioscler Thromb 1993; 13:1334-45.

Thorne RF, et al. CD36 is a receptor for oxidized high density lipoprotein: implications for the development of atherosclerosis. FEBS Lett 2007; 581:1227-32.

Vlieghe P, et al. Synthetic therapeutic peptides: science and market. Drug Discov Today 2010; 15:40-56.

Cormode DP, et al. An ApoA-I mimetic peptide high-density-lipoprotein-based MRI contrast agent for atherosclerotic plaque composition detection. Small 2008; 4:1437-44.

Briley-Saebo KC, et al. Targeted molecular probes for imaging atherosclerotic lesions with magnetic resonance using antibodies that recognize oxidation-specific epitopes. Circulation 2008; 117:3206-15.

Cormode DP, et al. Atherosclerotic plaque composition: analysis with multicolor CT and targeted gold nanoparticles. Radiology 2010; 256:774-82.

Platt N, Gordon S. Is the class A macrophage scavenger receptor (SR-A) multifunctional?—The mouse's tale. J Clin Invest 2001; 108:649-54.

Bergt C, et al. The myeloperoxidase product hypochlorous acid oxidizes HDL in the human artery wall and impairs ABCA1-dependent cholesterol transport. Proc Natl Acad Sci U S A 2004; 101:13032-7.

Marten K, Hansell DM. Imaging of macrophage-related lung diseases. Eur Radiol 2005; 15:727-41.

International Search Report dated Jul. 29, 2011, received in PCT/US2010/052117.

\* cited by examiner

METHODS AND COMPOSITIONS FOR TARGETED DELIVERY

CROSS-REFERENCE TO A RELATED APPLICATION

This application is a continuation-in-part application of International Patent Application Serial No. PCT/US10/52117, entitled "METHODS AND COMPOSITIONS FOR TARGETED IMAGING", filed on Oct. 10, 2010, which claims priority to U.S. provisional application Ser. No. 61/250,465, filed on Oct. 9, 2009, entitled "Methods and Compositions for Targeted Imaging". The entire content of the aforementioned applications is incorporated herein by reference.

FIELD OF THE INVENTION

The present invention relates to a composition comprising a therapeutic agent covalently or noncovalently conjugated to lipoprotein nanoparticles. The invention further relates to the use of the composition for the targeted drug delivery in the treatment or prevention of multiple disorders.

BACKGROUND OF THE INVENTION

1. Cancer and Tumor-Associated Macrophages

Despite advances in chemotherapy, cancer is one of the major causes of mortality in the United States, and the worldwide incidence of cancer continues to increase. Breast cancer remains the most common non-skin cancer and the leading cause of death in women. There is an unmet clinical need for an effective treatment of cancer.

The infiltrate of most tumors contains tumor-associated macrophages (TAMs) that are derived from circulating monocytic precursors and are directed into the tumor by chemokines Macrophages are prominent in the stromal compartment of virtually all types of malignancy and play an important role in tumor growth and metastasis. They secret a variety of growth factors, cytokines, chemokines, and enzymes that regulate tumor growth, angiogenesis, invasion, and metastasis. There is a significant positive correlation between high vascular grade and increased macrophage index, and a strong relationship is observed between increased macrophage counts and reduced relapse-free survival and reduced overall survival as an independent prognostic variable in cancer patients. The increased tumor islet macrophage density confers a marked survival advantage, whereas increased number of macrophages in the tumor stroma is associated with poor prognosis in lung cancer. Importantly, paclitaxel (PTX), a mitotic inhibitor widely used in cancer chemotherapy, induces TAM production of interleukin-12, a cytokine known to induce tumor regression and cure in animal model systems. Thus, the critical feature of PTX as an anticancer agent may not be only its microtubule-stabilizing activity, but also its ability to stimulate release of anticancer cytokines from TAMs. Also, targeting tumor-associated fibroblasts is known to improve cancer chemotherapy by increasing intratumoral drug uptake. Collectively, these data support targeting TAMs as a novel strategy of not only cancer imaging but also therapy of cancer.

2. Atherosclerosis, Restenosis, and Macrophages

Despite advances in cardiovascular care, atherosclerosis, the buildup of plaque in the artery walls, remains the leading cause of death in the United States. Inflammation has a crucial role at all stages of atherosclerosis. Macrophages are involved in the formation, progression, and pathogenicity of atherosclerotic plaques. Further, after percutaneous coronary interventions (angioplasty or stent implantation), restenosis remains to be a problem in clinical cardiology. In this field, nanoparticle technology is regarded as a promising approach to deliver antiproliferative and antiremodeling drugs at the site of injury. Thus, in atherosclerosis and restenosis, macrophages are an attractive target for delivery of not only imaging agents (PCT Pat Appl PCT/US10/52117) but also therapeutics (US Pat Appl 20060257466 and U.S. Pat. No. 7,740,854).

3. Other Diseases and Macrophages

In bacterial infectious diseases, macrophage-specific delivery systems are particularly attractive because macrophages act as host cells for many parasites and bacteria that give rise to the outbreak of so many deadly diseases. Besides the advent of other classical drugs carriers, polymeric nanoparticles have been explored for their effective use in experimental infectious diseases upon macrophage targeting.

In acquired immune deficiency syndrome (AIDS) therapy, macrophages could be targeted since they represent a cell population of the reticuloendothelial system (RES) that plays an important role in the immunopathogenesis of the disease. Increasing drug concentrations at specific sites where macrophages are abundant may allow a reduction in the dosage and, as a result, a decrease in systemic toxicity.

4. Lipoprotein Particles as Delivery Vehicles for Therapeutic Agents

The use of non-viral nanoparticulate systems for the delivery of therapeutic agents is receiving considerable attention for medical and pharmaceutical applications. The increasing interest results from the fact that these systems can be designed to meet specific physicochemical requirements, and they display low toxic and immunogenic effects. Among potential cellular targets by drug-loaded nanoparticles, macrophages are considered because they play a central role in inflammation and they act as reservoirs for microorganisms that are involved with deadly infectious diseases. The most common and potent drugs used in the treatment of cancer, bacterial infectious diseases, and other macrophage-mediated diseases often induce unwanted side effects, when applied as a free form, due to the necessity of high doses to induce a satisfactory effect. This could result in their systemic spreading, a lack of bioavailability at the desired sites, and a short half-life. Therefore, the use of drug-loaded nanoparticles represents a good alternative to avoid, or at least decrease, side effects and increase efficacy.

Lipoprotein particles (lipoproteins) have been used previously as delivery vehicles for drugs (U.S. Pat. Nos. 6,306,433, 7,824,709 and 6,514,523; US Pat Appl 20090110739). Lipoproteins are the native transporters in the circulation of a variety of lipophilic and hydrophilic compounds and are classified into four main categories depending on size and composition (i.e., in order of decreasing diameter: chylomicrons, very low density lipoproteins (VLDL), low- and high-density lipoproteins (LDL and HDL, respectively). With the exception of HDLs, the lipoproteins suffer the same drawbacks as micelles, conventional emulsions and liposomes, in that the entities are too large to serve as good vehicles for the delivery of therapeutic agents. In comparison to other drug delivery platforms, HDL or HDL-like lipoprotein particles have several advantages: 1) the protein constituent of HDL, apolipoprotein (apo) A-I, is an endogenous protein component and does not trigger immunoreactions, 2) the small size of the HDL particle (8-12 nm) allows to pass through blood vessel walls, 3) the small particle size also allows for intravenous, intramuscular and subcutaneous applications, and 4) a variety of therapeutic and imaging agents can be incorporated into this platform (U.S. Pat. Nos. 6,306,433, 7,824,709 and 6,514,523; US Pat Appls 20070243136 and 20090110739; PCT Pat Appl PCT/US10/52117). There has been increased activity in the patenting of lipoprotein-like formulations in the last several years, primarily with the aim of developing enhanced delivery vehicles for therapeutics and diagnostics.

Synthetic HDL (recombinant, or reconstituted HDL; rHDL) have been used as a vehicle for tumor-targeted delivery of PTX (US Pat Appl 20090110739). One of the major limitations of the suggested PTX-rHDL formulations includes low specificity of drug delivery to the tumor in vivo. The uptake of PTX from drug-loaded rHDL particles is facilitated by the scavenger receptor B type I (SR-BI), the receptor that is found in numerous cell types/tissues, including the liver and adrenal. Also, delivery of therapeutic agents by these particles to the tumor strongly depends on SR-BI expression level on cancer cells that may differ in various types of cancer and for patients at different stages of cancer.

5. An Unmet Need

Therefore, there is a need for a macrophage-targeted delivery vehicle that can freely enter macrophage-rich sites of interest, such as atherosclerotic plaques or tumor sites, and that increases drug concentrations at these sites. This agent should possess a high affinity for macrophages and their components in order to significantly reduce the therapeutic agent dosage required, thus limiting concerns related to systemic toxicity. This is especially important for anticancer chemotherapeutic agents most of which are lipophilic and thus cannot be administered by themselves as pure chemicals. These agents have to be included in biocompatible formulations to enhance solubility, increase circulatory residence time of the therapeutic agent, minimize the undesirable side effects and to alleviate drug resistance.

SUMMARY OF THE INVENTION

The present teachings disclose various nanoparticles that contain chemically and/or enzymatically modified apolipoproteins and are used for the targeted delivery of a therapeutic agent. The compositions of the present teachings include, but are not limited to, a synthetic nanoparticle, the synthetic nanoparticle comprising at least one chemically and/or enzymatically modified apolipoprotein A-I and/or A-II, at least one amphipathic lipid, and at least one therapeutic agent attached to said nanoparticle by a means selected from the group consisting of adsorption, incorporation, covalent bonding, chelating, and encapsulation. While the size of the nanoparticles is preferably between 5 nm and 25 nm, the diameter may be up to 150 nm. The disclosed nanoparticles may be spherical, discoidal or a distorted disc shape, e.g., ellipsoidal. In one aspect, a chemotherapeutic drug, including but not limiting to, doxorubicin, doxorubicin derivatives, paclitaxel, as well as any combination of these agents, may be attached to said nanoparticle for the tumor-targeted delivery in the treatment of cancer. In another aspect, the teachings provides a method and composition of targeted delivery of therapeutic agents in treating atherosclerosis and restenosis. In yet another aspect, the teachings provide a method and composition of the targeted delivery of therapeutic agents in treating bacterial infectious diseases.

Therefore, further disclosed herein is a synthetic nanoparticle. The synthetic nanoparticle comprises at least one modified apolipoprotein, at least one lipid; and at least one therapeutic agent. The therapeutic agent is attached to the nanoparticle by a means selected from the group consisting of adsorption, incorporation, covalent bonding, chelating, and encapsulation. The synthetic nanoparticle is discoidal or spherical in shape and has a diameter of from about 5 nm to about 150 nm. The modified apolipoprotein of the nanoparticle may contain at least one amino acid residue which is chemically or enzymatically modified. The modified apolipoprotein may be an oxidized apolipoprotein. The oxidized apolipoprotein may contain at least one amino acid residue which is oxidized. The oxidized residue may be a methionine. The modified apolipoprotein may contain at least one amino acid residue which is oxidized, halogenated, or nitrated. The modified apolipoprotein may include an amphipathic apolipoprotein or a fragment thereof. The modified apolipoprotein may include a modified apolipoprotein A-I, A-II, A-IV, B, C-I, C-II, C-III, or E. In another aspect, the synthetic nanoparticle may comprise any protein. The protein may comprise apolipoprotein A-I, A-II, A-IV, B, C-I, C-II, C-III, or E. In yet another aspect, the synthetic nanoparticle may comprise a targeting moiety to enhance the targeting efficacy of the therapeutic agent. The targeting moiety may include a protein, a polypeptide, an antibody, a receptor, a ligand, a peptidomimetic agent, an aptamer or a product of phage display. In still another aspect, the synthetic nanoparticle may comprise a therapeutic agent selected from the group anticancer, antibacterial, antiviral, autoimmune, anti-inflammatory and cardiovascular agents, antioxidants, therapeutic peptides. The therapeutic agent may also be selected from the group comprising paclitaxel, valrubicin, doxorubicin, taxotere, campotechin, etoposide, and any combination thereof. The lipid of the synthetic nanoparticle may include cholesterol, a cholesteryl ester, a phospholipid, a glycolipid, a sphingolipid, a cationic lipid, a diacylglycerol, or a triacylglycerol. And further, the phospholipid may include phosphatidylcholine (PC), phosphatidylethanolamine (PE), phosphatidylserine (PS), phosphatidylinositol (PI), phosphatidylglycerol (PG), cardiolipin (CL), sphingomyelin (SM), or phosphatidic acid (PA). And even further, the cationic lipid can be 1,2-dioleoyl-3-trimethylammonium-propane (DOTAP). The lipid of the synthetic nanoparticle may be polyethylene glycol(PEG)ylated.

The disclosure further provides for a method of making a synthetic nanoparticle. The method comprises co-dissolving a predetermined amount of a mixture of neutral and/or charged lipids with a predetermined amount of a therapeutic agent and a predetermined amount of modified apolipoprotein. The co-dissolving is conducted for a time period sufficient to allow the mixture to coalesce into structures whereby particles are formed incorporating the therapeutic agent. The method further comprises isolating structures that have a size of between about 5 to about 50 nm diameter. The lipid of the method may include PC, PE, PS, PI, PG, CL, SM, DOTAP or PA. The modified apolipoprotein of the method may include modified apolipoprotein A-I, A-II, A-IV, B, C-I, C-II, C-III, or E.

The disclosure also provided for a method of making a synthetic nanoparticle comprising co-dissolving a predetermined amount of a mixture of neutral and/or charged lipids with a predetermined amount of cholesterol, a predetermined amount of HDL core lipids comprising triglycerides and/or cholesteryl ester, and a predetermined amount of a therapeutic agent. The method further comprises drying the mixture under nitrogen. The method even further comprises co-dissolving the dried mixture of with a predetermined amount of sodium cholate and a predetermined amount of modified apolipoprotein. The co-dissolving is conducted for a time period sufficient to allow the components to coalesce into structures. The method still further comprises removing sodium cholate from the mixture, and isolating structures that have a size of between about 5 to about 100 nm diameter. The lipid of the method may include PC, PE, PS, PI, PG, CL, SM, DOTAP, or PA. The modified apolipoprotein of the method may include modified apolipoprotein A-I, A-II, A-IV, B, C-I, C-II, C-III, or E.

The disclosure also provides for a method of generating a therapeutic agent-incorporated synthetic nanoparticle. The method comprises co-dissolving a predetermined amount of a lipid with a predetermined amount of cholesterol, a predetermined amount of modified apolipoprotein, and a predetermined amount of a therapeutic agent. The co-dissolving is conducted for a time period sufficient to allow the mixture to coalesce into structures whereby particles are formed incorporating the therapeutic agent. The method further comprises isolating structures that have a size of between about 5 to about 150 nm diameter. The lipid of the method may comprise DOTAP. The modified apolipoprotein of the method may include modified apolipoprotein A-I, A-II, A-IV, B, C-I, C-II, C-III, or E.

The disclosure also provides for a method of treating a macrophage-related condition. The method comprises providing a composition comprising a synthetic nanoparticle of the present disclosure, a patient having at least one symptom of a disease or condition in which macrophages are involved or recruited, and administering the composition to the patient under conditions such that said one symptom is reduced. The macrophage-related condition of the method may include a heart disease, peripheral artery disease, restenosis, stroke, the cancers (e.g., sarcoma, lymphoma, leukemia, carcinoma and melanoma), bacterial infectious diseases, acquired immune deficiency syndrome (AIDS), allergic diseases, autoimmune diseases (e.g., rheumatoid arthritis, Sjogrens, scleroderma, systemic lupus erythematosus, non-specific vasculitis, Kawasaki's disease, psoriasis, type I diabetes, pemphigus vulgaris), granulomatous diseases (e.g., tuberculosis, sarcoidosis, lymphomatoid granulomatosis, Wegener's granulomatosus), Gaucher's disease, inflammatory diseases (e.g., sepsis, inflammatory lung diseases such as interstitial pneumonitis and asthma, inflammatory bowel disease such as Crohn's disease, and inflammatory arthritis), and transplant (e.g., heart/lung transplants) rejection reactions.

BRIEF DESCRIPTION OF THE FIGURES

The following figures form part of the present specification and are included to further illustrate aspects of the present invention. The invention may be better understood by reference to the figures in combination with the detailed description of the specific embodiments presented herein.

DETAILED DESCRIPTION OF THE INVENTION

Definitions

Figure 1:
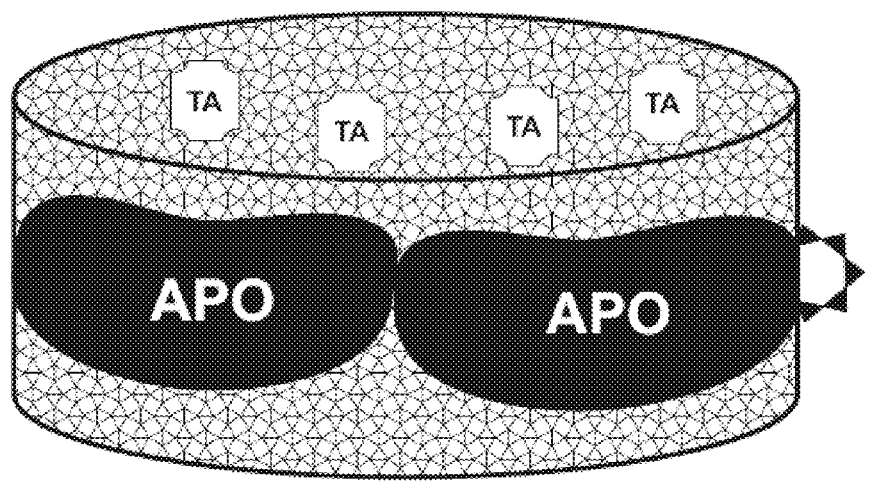
FIG. 1 presents a schematic representation of one embodiment of a discoidal composition of the present invention with a therapeutic agent attached to said composition.

The terms "APOA1_HUMAN", "Apolipoprotein A-1", "Apolipoprotein A-1", "APOA1", "ApoA-I", "Apo-AI", "ApoA-1", "apo-A1", "apoA-1" and "Apo-A1" refer to the naturally occurring human protein listed in the UniProt Knowledgebase (UniProtKB, www.uniprot.org) under the name "APOA1_HUMAN". The protein amino acid sequence can be found under the entry UniProt KB/Swiss-Prot P02647 (www.uniprot.org/uniprot/P02647). The terms "APOA2_HUMAN", "Apolipoprotein A-II", Apolipoprotein A-2", "APOA2", "ApoA-II", "Apo-AII", "ApoA-2", "apo-A2", "apoA-2" and "Apo-A2" refer to the naturally occurring human protein listed in the UniProt Knowledgebase (UniProtKB, www.uniprot.org) under the name "APOA2_HUMAN". The protein amino acid sequence can be found under the entry UniProt KB/Swiss-Prot P02652 (http://www.uniprot.org/uniprot/P02652).

As employed herein and understood by the ordinary skill in the art, the term "recombinant protein" describes the protein obtained from bacterial or other sources using the recombinant DNA technology. Furthermore, a suffix or a prefix indicating the species from which the protein is derived is added to the protein's name when a non-human protein such as non-human apo A-I or apo A-II is described (U.S. Pat. No. 6,953,840; http://www.uniprot.org/uniprot/Q00623; http://www.uniprot.org/uniprot/P09813). In special cases, a suffix or a prefix may also indicate a well-known apoA-1 variant, e.g. apo A-I Milano (U.S. Pat. No. 7,435,717). As used herein, the term "aptamer" or "specifically binding oligonucleotide" refers to an oligonucleotide that is capable of forming a complex with an intended target substance.

In the present disclosure, the term "modified protein" is used to describe chemically or enzymatically, or chemically and enzymatically modified oligopeptides, oligopseudopeptides, polypeptides, pseudopolypeptides, and native proteins (synthetic or otherwise derived), regardless of the nature of the chemical and/or enzymatic modification. The term "pseudopeptide" refers to a peptide where one or more peptide bonds are replaced by non-amido bonds such as ester or one or more amino acids are replaced by amino acid analogs. The term "peptides" refers not only to those comprised of all natural amino acids, but also to those which contain unnatural amino acids or other non-coded structural units. The terms "peptides", when used alone, include pseudopeptides. It is worth mentioning that "modified proteins" have utility in many biomedical applications because of their increased stability against in vivo degradation, superior pharmacokinetics, and altered immunogenicity compared to their native counterparts.

The term "modified protein," as employed herein, also includes oxidized proteins. The term "oxidized protein" refers to a protein in which at least one amino acid residue is oxidized. The term "oxidized protein fragment" refers to a protein fragment in which at least one amino acid residue is oxidized. The term "oxidation status" refers to a metric of the extent to which specific amino acid residues are replaced by corresponding oxidized amino acid residues in a protein or a protein fragment. The term "extent of oxidation" refers to the degree to which potentially oxidizable amino acids in a protein or fragment have undergone oxidation. For example, if the protein fragment contains a single tyrosine residue which is potentially oxidized to 3-chlorotyrosine, then an increase in mass of about 34 Dalton (i.e., the approximate difference in mass between chlorine and hydrogen) indicates oxidation of tyrosine to 3-chlorotyrosine. Similarly, if the protein fragment contains a single methionine residue which is potentially oxidized to methionine sulfoxide, then an increase in mass of 16 Dalton (i.e., the difference in mass between methionine and methionine containing one extra oxygen) indicates oxidation of methionine to methionine sulfoxides.

The oxidation status can be measured by metrics known to the arts of protein and peptide chemistry (US Pat Appl 20080020400; US Pat Appl 20050239136) including, without limitation, assay of the number of oxidized residues, mass spectral peak intensity, mass spectral integrated area, and the like. In some embodiments of any of the aspects provided herein, oxidation status is reported as a percentage, wherein 0% refers to no oxidation and 100% refers to complete oxidation of potentially oxidizable amino acid residues within apo A-I or apo A-II or fragments thereof. The term "potentially subject to oxidation," "potentially oxidizable amino acid residues", and the like refer to an amino acid which can undergo oxidation, for example by nitration or chlorination.

The term "encapsulation" as used herein refers to the enclosure of a molecule, such as a contrast agent or therapeutics, inside the nanoparticle. Such encapsulation may be generated, according to an embodiment, by synthesis of nanoparticles in the presence of a liquid solution containing a contrast agent or therapeutics. The term "incorporation" as used herein refers to imbibing or adsorbing the contrast agent or therapeutics onto the nanoparticle. The terms "reconstituted" and "recombinant" as used herein both refer to synthetic HDL-type particles that represent both discoidal and spherical nanoparticles.

A "site of interest" on a target as used herein is a site to which modified proteins and protein fragments of the present invention bind. The term "target site", as used herein, refers to sites/tissue areas of interest. As used in this invention, the terms "target cells" or "target tissues" refer to those cells or tissues, respectively that are intended to be targeted using the compositions of the present invention delivered in accord with the invention. Target cells or target tissues take up or link with the modified proteins or protein fragments of the invention. Target cells are cells in target tissue, and the target tissue includes, but is not limited to, atherosclerotic plaques, vascular endothelial tissue, abnormal vascular walls of tumors, solid tumors, tumor-associated macrophages, and other tissues or cells related to cancer, cardiovascular, inflammatory, autoimmune diseases, and the like. Further, target cells include virus-containing cells, and parasite-containing cells. Also included among target cells are cells undergoing substantially more rapid division as compared to non-target cells. The term "target cells" also includes, but is not limited to, microorganisms such as bacteria, viruses, fungi, parasites, and infectious agents. Thus, the term "target cell" is not limited to living cells but also includes infectious organic particles such as viruses. "Target compositions" or "target biological components" include, but are not be limited to: toxins, peptides, polymers, and other compounds that may be selectively and specifically identified as an organic target that is intended to be visualized in imaging techniques using the compositions of the present invention. The term "therapeutic agent" or "drug" as used herein refers to any compound or composition having preventive, therapeutic or diagnostic activity, primarily but not exclusively in the treatment of patients with macrophage-related diseases. The terms "macrophage-associated", "macrophage-mediated", and "macrophage-related diseases" include diseases associated with macrophages (U.S. Pat. No. 7,740,854 and PCT Pat Appl PCT/US10/52117). The term "plaque" includes, for example, an atherosclerotic plaque.

Detailed Description

Because of the leading position of cancer as a cause of mortality in industrialized societies, applications in this area are thus highlighted. However, it should be noted that the techniques and compositions listed and described below are applicable to a broad range of disease states including, but not limiting to, cardiovascular disease, bacterial infectious diseases, diabetes, and autoimmune diseases. Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

As well-known in the art and described in US Pat Appl 20090110739, most anticancer chemotherapeutic agents cannot be administered by themselves as pure chemicals but have to be included in biocompatible formulations to enhance solubility, increase circulatory residence time of the therapeutic agent (TA), minimize the undesirable side effects and alleviate drug resistance. Numerous formulation approaches have been developed, including solid lipid particles, emulsions, liposomes, etc., however, the delivery of the poorly water soluble (hydrophobic, or lipophilic) pharmaceuticals remains especially problematic as most of the body compartments, including the blood circulation and intracellular fluids, represent an aqueous environment. As a result, the direct injection of hydrophobic TAs often results in harmful side effects due to hypersensitivity, hemolysis, cardiac and neurological symptoms. Consequently, there is need for more effective formulations of hydrophobic drugs to improve their targeted delivery, biocompatibility and therapeutic efficiency.

Chemical or enzymatic modification of fully assembled HDL particles enhances their absorption by the macrophages. However, in the modified HDL particle both, the protein and the lipid portion of the particle can undergo the chemical modification. The prior art (U.S. Pat. Nos. 6,306,433, 7,824,709, and 6,514,523; US Pat Appls 20090110739 and 20070243136) neither suggests nor teaches one of ordinary skill in the art to investigate the drug delivery performance of HDL particles in which only the apolipoprotein portion has been chemically altered.

As described herein, it is surprisingly found that oxidative modification of only protein constituents or peptide fragments thereof of HDL is sufficient to convert these particles to substrates for macrophage scavenger receptors and provide targeted delivery, biocompatibility and therapeutic efficiency of TAs. Compositions of the invention are synthetic HDL or HDL-like particles, protein constituents of which, apolipoproteins (apo) A-I and/or A-II or fragments thereof are modified. Certain controlled chemical or enzymatic modification of apo A-I or A-II or fragments thereof converts these apolipoproteins to substrates for macrophage scavenger receptors and results in the improvement of association of the TA-(HDL/modified apolipoprotein)-particle with macrophages and/or absorption (uptake) of the TA-(HDL/modified apolipoprotein)-particle by macrophages when compared to that of the TA-(HDL/apolipoprotein)-particle constructed with non-modified naturally occurring apo A-I, apo A-II or fragments thereof. These advantageous compositions are demonstrated by the present invention to solve numerous problems which otherwise are associated with high dosages of TAs required and the lack of control and reproducibility of formulations, especially in large-scale production.

A. Apolipoproteins and Apolipoprotein Peptides

In the methods of the present invention, the lipoproteins of interest are HDLs and their synthetic reconstituted analogues. The functional characteristics of HDL particles are mainly determined by their major protein components such as apo A-I and A-II. Each HDL particle usually comprises at least 1 molecule, and usually 2 to 4 molecules, of apo A-I.

The nature of the apolipoproteins comprising the protein fraction of the compositions of the present invention is not critical for success as described in PCT Pat Appl PCT/US10/52117. Examples of suitable apolipoproteins include, but are not limited to, preproapolipoprotein forms of apo A-I and apo A-II; pro- and mature forms of human apo A-I and apo A-II; and active polymorphic forms, isoforms, variants and mutants as well as truncated forms, the most common of which are apo A-I$_{Milano}$ and apo A-I$_P$, as disclosed in US Pat Appl 20060217312. Apolipoproteins mutants containing cysteine residues are also known, and can also be used (see, e.g., US Pat Appl 20030181372). The apolipoproteins may be in the form of monomers or dimers, which may be homodimers or heterodimers. For example, homo- and heterodimers (where feasible) of pro- and mature apo A-I, apoA-I$_{Milano}$, apoA-I$_P$, and apo A-II may be used. The apolipoproteins may include residues corresponding to elements that facilitate their isolation, such as His tags, or other elements designed for other purposes, so long as the apolipoprotein retains some biological activity when included in a complex.

As it is well-known in the art, such apolipoproteins can be purified from animal sources (and in particular from human sources) or produced recombinantly (PCT Pat Appl PCT/US10/52117, U.S. Pat. Nos. 5,059,528, 5,128,318, 6,617,134, and U.S. Pat Appls 20020156007, 20040067873, 20040077541, and 20040266660).

Non-limiting examples of peptides and peptide analogs that correspond to apo A-I, apo A-I$_{Milano}$, and apo A-II, and are suitable for enzymatic and/or chemical modifications and subsequent use as peptide fragments of modified apolipoproteins in the complexes and compositions described herein are disclosed in U.S. Pat. Nos. 6,004,925, 6,037,323 and 6,046,166, U.S. Pat. No. 5,840,688, US Appls 20040266671, 20040254120, 20030171277, 20030045460, 20030087819, and 20060217312. These peptides and peptide analogues can be composed of L-amino acid or D-amino acids or mixture of L- and D-amino acids. They may also include one or more non-peptide or amide linkages, such as one or more well-known peptide/amide isosteres. Such "peptide and/or peptide mimetic" apolipoproteins can be synthesized or manufactured using any technique for peptide synthesis known in the art, including, e.g., the techniques described in U.S. Pat. Nos. 6,004,925, 6,037,323 and 6,046,166.

The complexes and compositions of the present invention may include a single type of apolipoprotein and/or peptide fragments thereof, or mixtures of two different apolipoproteins and peptide fragments thereof, which may be derived from the same or different species. Although not required, the charged lipoprotein complexes will preferably comprise apolipoproteins that are derived from, or correspond in amino acid sequence to, the animal species being treated, in order to avoid inducing an immune response to the therapy. The use of peptide mimetic apolipoproteins may also reduce or avoid an immune response.

B. Modified Apolipoproteins and Apolipoprotein Peptides

For the compositions of the present invention, it is critical that the prepared nanoparticles contain at least one modified molecule of apo A-I and/or apo A-II and/or fragments thereof (FIGS. 1, 2A, 2B) described herein. Although it is not necessary to understand the mechanism of an invention, it is believed that being incorporated into the compositions of the present invention, the modified apo A-I and/or apo A-II and/or fragments thereof in addition to keeping the structural integrity of the nanoparticles of the invention, also target the nanoparticles to sites of interest such, for example, as atherosclerotic plagues or tumor sites.

Figure 4:
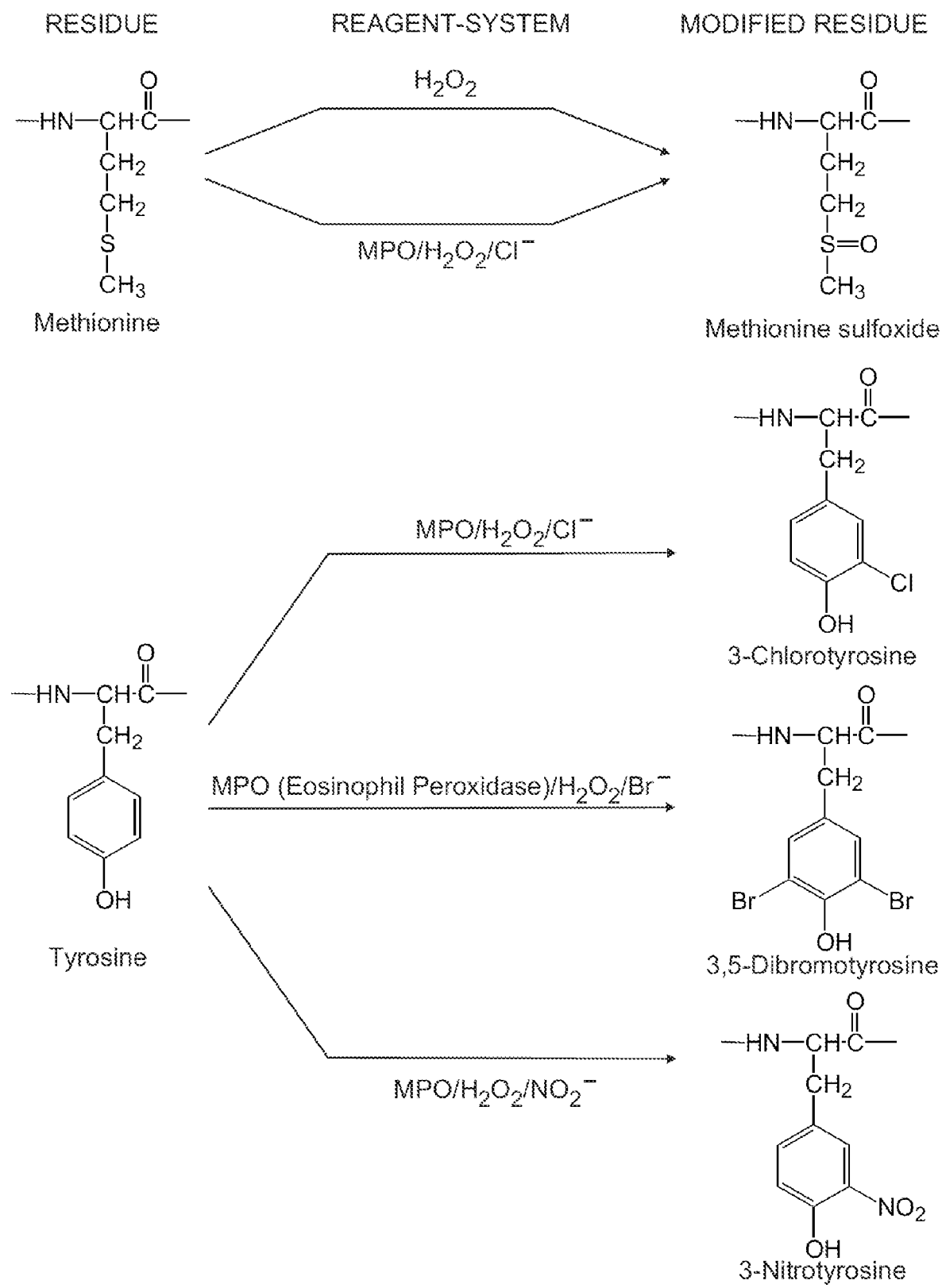
FIG. 4 contains examples of naturally occurring chemical and enzymatic modifications of amino acid residues of proteins including, but not limiting to, apolipoproteins of the present invention and fragments thereof. Abbreviation used: MPO—myeloperoxidase.

In preferred embodiments, the modified apolipoprotein is selected from a modified apo A-I or a fragment thereof and a modified apo A-II or a fragment thereof. In preferred embodiments, the modified apolipoprotein is any combination of a modified apo A-I and a modified A-II and fragments thereof. In still preferred embodiments, a modified apo A-I is an oxidized apo A-I or an oxidized apo A-I fragment that comprises one or more of the following amino acid residues: 3-chlorotyrosine, 3-nitrotyrosine, 3,5-dibromotyrosine, dityrosine, trihydroxyphenylalanine, dihydroxyphenylalanine, methionine sulfoxide, and tyrosine peroxide, or any combination thereof. FIG. 4 shows examples of such modified amino acid residues. In still other preferred embodiments, a modified apo A-II is an oxidized apo A-II or an oxidized apo A-II fragment that comprises one or more of the following amino acid residues: methionine sulfoxide, trihydroxyphenylalanine, dihydroxyphenylalanine, 3-chlorotyrosine, 3-nitrotyrosine, 3,5-dibromotyrosine, dityrosine, and tyrosine peroxide, or any combination thereof.

Figure 5:
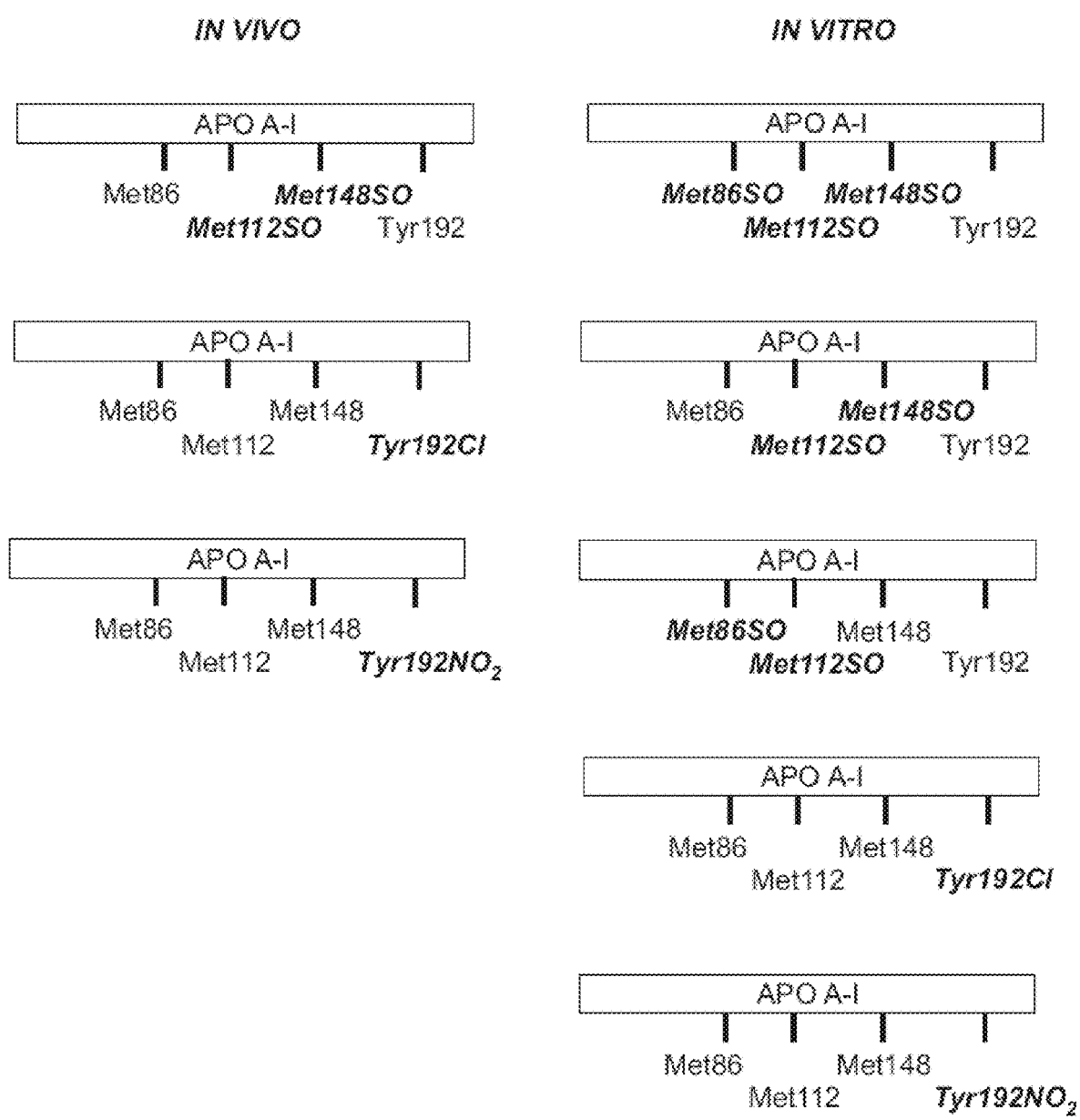
FIG. 5 presents a schematic representation of several modifications of apolipoprotein (apo) A-I naturally occurring in vivo and artificially produced in vitro. While not being bound to any particular theory, it is believed that Met residues at positions 112 and 148 are the major sites of sulfoxidation by hydrogen peroxide alone or in combination with myeloperoxidase in vivo, whereas sulfoxides of all three Met residues of apo A-I can be produced in different combinations in vitro, depending on the oxidant used. It is also believed that Tyr residue at the position 192 is the major of nitration and chlorination by myeloperoxidase in vivo and in vitro.
Figure 6:
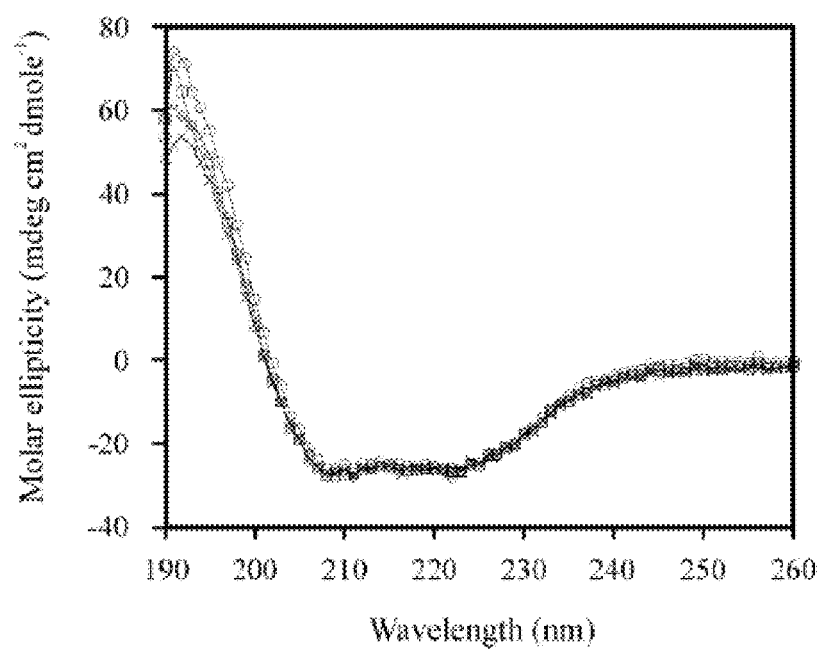
FIG. 6 presents the exemplary data showing far-UV circular dichroism spectra of apo A-I on different rHDL particles. The spectra of lipid-associated apo A-I in rHDL-1 (open circles), rHDL-2 (open squares), rHDL-3 (open diamonds) and rHDL-4 (crossings) are shown.
Figure 7:
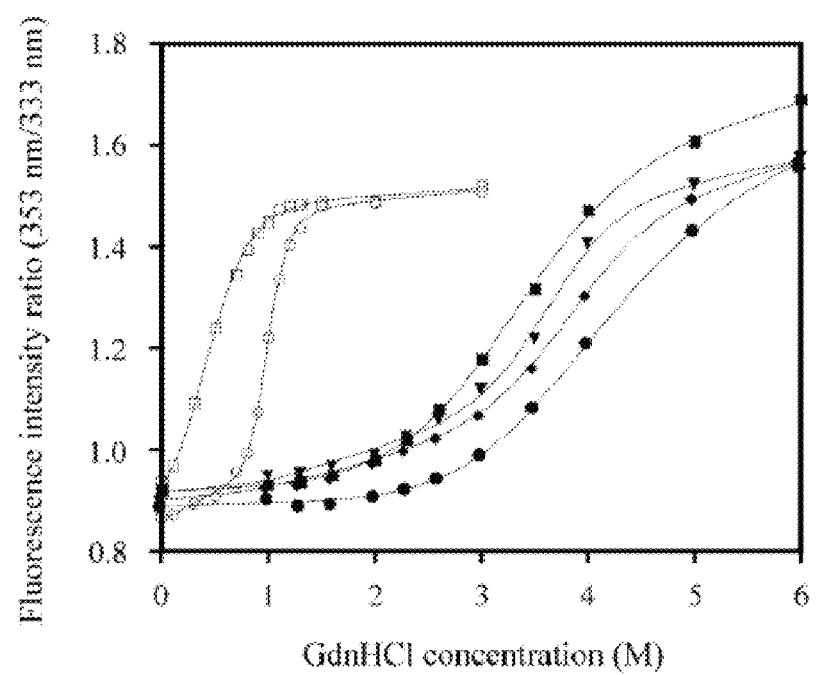
FIG. 7 presents the exemplary data showing denaturation of lipid-free apo A-I and rHDL complexes by GdnHCl. Aliquots of unoxidized (open circles) and oxidized (open squares) lipid-free apo A-I proteins or prepared rHDL-1 (filled circles), rHDL-2 (filled squares), rHDL-3 (filled diamonds) and rHDL-4 (filled upside-down triangles) complexes were incubated at 4° C. with 0-6 M GdnHCl in 10 mM TBS, pH 7.4 for 72 h. The fluorescence intensities at 353 and 333 nm were measured with sample protein concentrations between 0.05 and 0.1 mg of protein/ml. The ratio of fluorescence intensity at 353 nm to that at 333 nm is plotted against the GdnHCl molar concentration.
Figure 8:
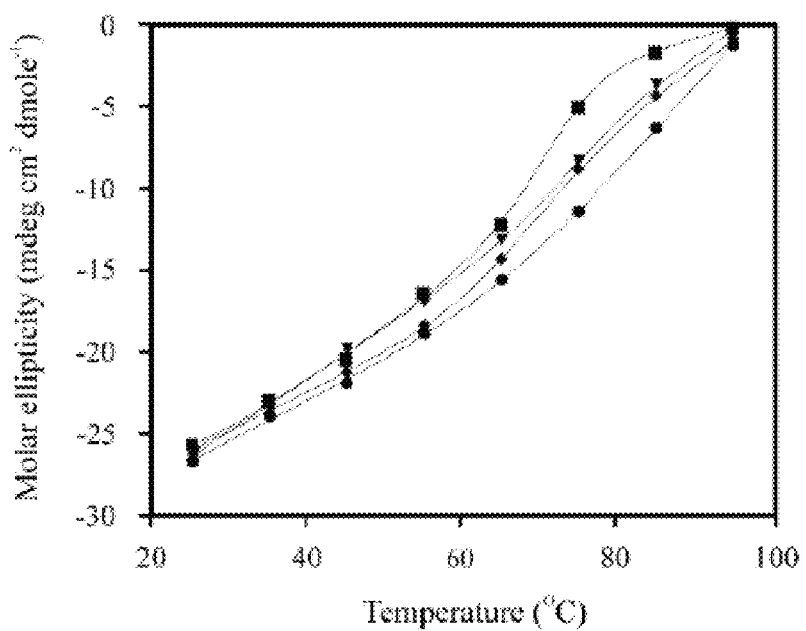
FIG. 8 presents the exemplary data showing temperature-induced unfolding of rHDL complexes. The circular dichroic data were collected on solutions of rHDL-1 (filled circles), rHDL-2 (filled squares), rHDL-3 (filled diamonds) and rHDL-4 (filled upside-down triangles).
Figure 9:
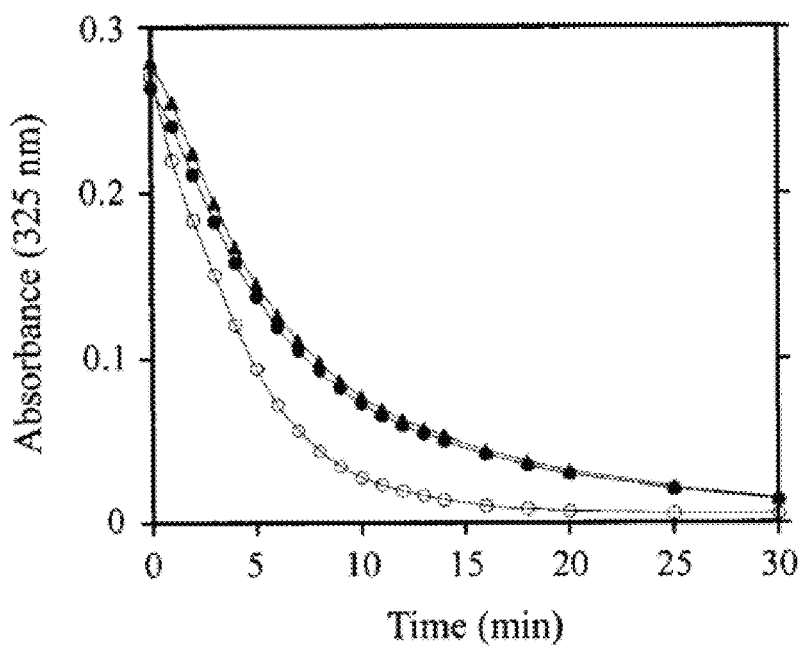
FIG. 9 presents the exemplary data showing 1,2-dimyristoyl-sn-glycero-3-phosphocholine (DMPC) kinetic binding with unoxidized, oxidized, and reduced apo A-I proteins.

Those of skill in the art are aware that apo A-I contains three methionines that can potentially undergo sulfoxidation, Met-86, Met-112, and Met-148 (FIG. 5). As well known in the art and described in PCT Pat Appl PCT/US10/52117, sulfoxidation of apo A-I methionines 112 and 148 occurs in vivo (FIG. 5) and affects many HDL functions including uptake by macrophages. This and other naturally occurring apo A-I modifications (e.g. tyrosine chlorination, bromination and nitrosylation; FIG. 5) can convert native HDL into a macrophage substrate (PCT Pat Appl PCT/US10/52117).

In particularly preferred embodiments, a modified apo A-I is an oxidized apo A-I or an oxidized apo A-I fragment that comprises methionine sulfoxide at any one of positions 86, 112, 148, or any combination of said positions (FIG. 5). In still particularly preferred embodiments, a modified apo A-II is an oxidized apo A-II or an oxidized apo A-II fragment that comprises methionine sulfoxide at position 26. In still preferred embodiments, apo A-I$_{unox}$ is unoxidized apo A-I contained in initial serum apo A-I. In other preferred embodiments apo A-II$_{unox}$ is unoxidized apo A-II contained in initial serum apo A-II. In other preferred embodiments, apo A-I$_{ox}$ is oxidized apo A-I (with sulfoxidized methionines at positions 112 and 148) contained in serum apo A-I or obtained from unoxidized apo A-I using hydrogen peroxide.

In certain embodiments, methionine sulfoxidation and the functional changes associated with the oxidation can be reversed by peptide methionine sulfoxide reductase (PMSR) in the presence of physiologically important universal antioxidant dihydrolipoic acid (DHLA) as a cofactor (PCT Pat Appl PCT/US10/52117). In preferred embodiments; apo A-I$_{red}$ is reduced apo A-I obtained by reduction of oxidized apo A-I (with sulfoxidized methionines at positions 112 and 148) using PMSR.

In preferred embodiments, apo A-I, apo A-II or fragments thereof are first chemically or enzymatically modified and then the synthetic nanoparticle of the invention is assembled using this modified apolipoprotein. It might be possible, however, to selectively modify only apolipoprotein portion of the fully assembled synthetic nanoparticle of the invention.

It is understood by those of ordinary skill in the art that the modified apo A-I and apo A-II molecules can be prepared and purified using the standard procedures well known in the art (see e.g. PCT Pat Appl PCT/US10/52117). It should be also understood by those of ordinary skill in the art that apo A-I and apo A-II peptide fragments containing modified amino acid residues can be easily synthesized or manufactured by any technique for peptide synthesis known in the art, including, e.g., the techniques described in U.S. Pat. Nos. 6,004,925, 6,037,323 and 6,046,166, and the modified peptides can be purified by any method known in the art, including high performance liquid chromatography (HPLC).

C. Reconstituted HDL

The preferred particles of the invention comprise at least one modified apo A-I and/or A-II or peptide fragments thereof and at least one amphipathic lipid, to form a structure that can be spherical or discoidal. The inclusion of an amphipathic apolipoprotein or peptide aids the structural stability of the particle, particularly when the particle has a discoidal shape. Exemplary proteins or peptides are selected from the major protein constituents of HDL, apo A-I and apo A-II, and peptide fragments thereof.

Figure 2A:
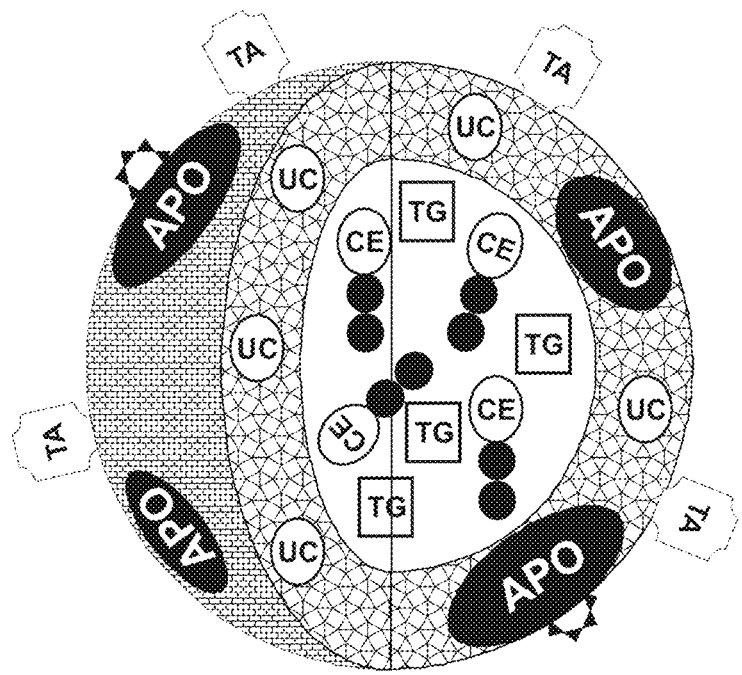
FIG. 2A presents a schematic representation of one embodiment of a spherical composition of the present invention with a therapeutic agent attached to said composition.
Figure 2B:
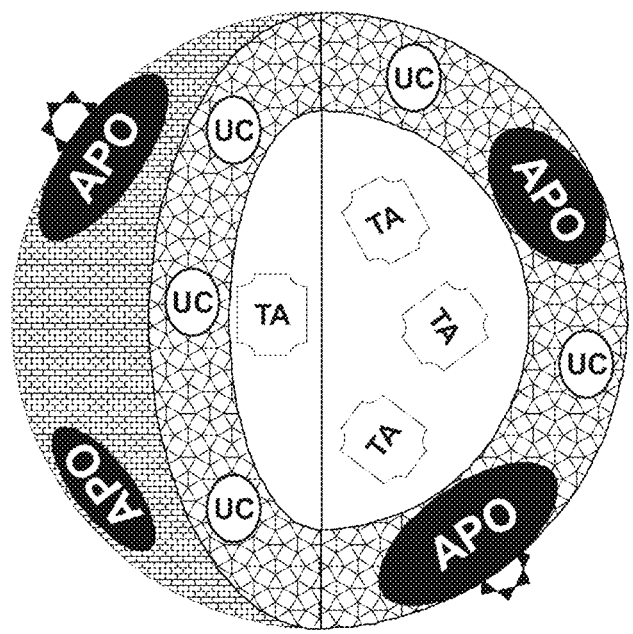
FIG. 2B presents a schematic representation of one embodiment of a spherical composition of the present invention with encapsulated therapeutic agents.
Figure 10:
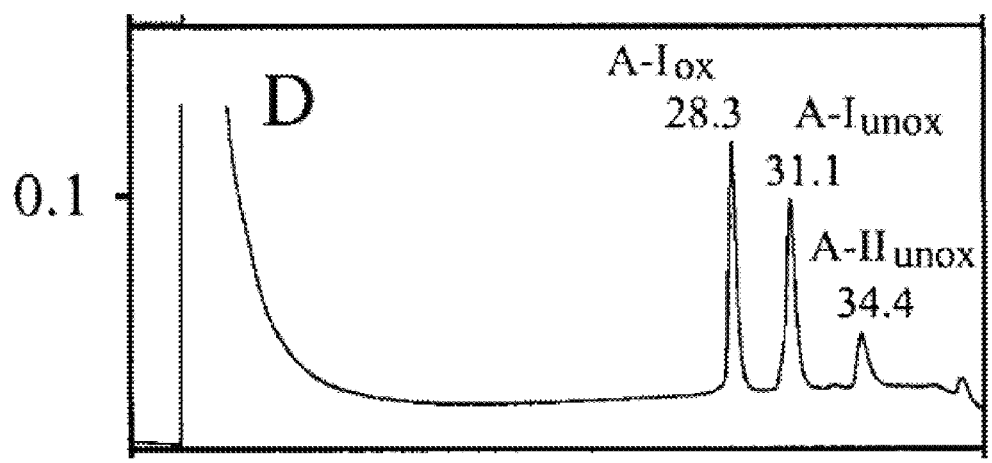
FIG. 10 presents the exemplary data showing an analytical reversed-phase HPLC profile of apo A-I in rHDL particles containing apo A-I$_{unox}$, apo A-I$_{ox}$, and apo A-H$_{unox}$ with a molar ratio of 3:3:1 (rHDL-4). The retention times (in minutes) are shown above each peak.
Figure 11:
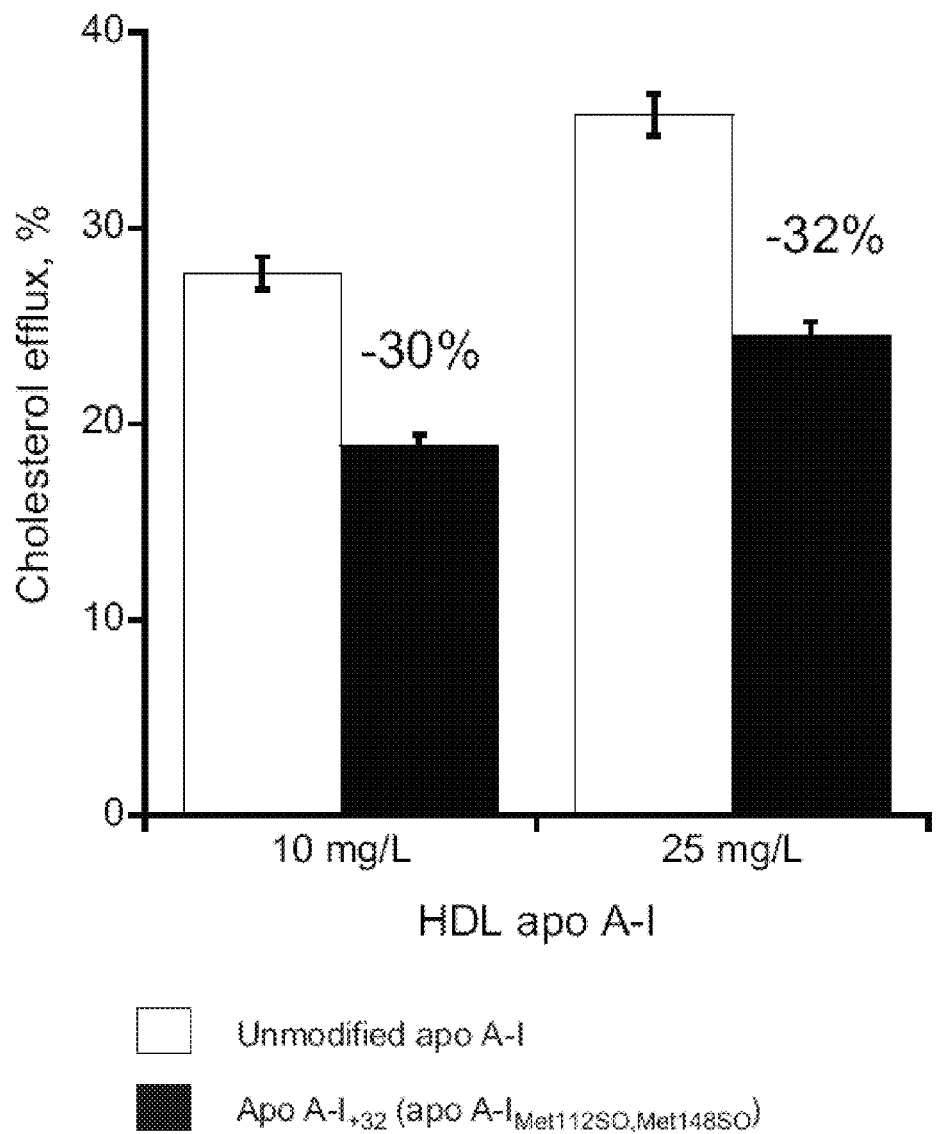
FIG. 11 presents the exemplary data showing observed values of relative cholesterol efflux from cholesterol-loaded human skin fibroblasts promoted by HDL containing unmodified (unoxidized) apo A-I (empty bars) and oxidized (apo A-I$_{-32}$, or apo A-I$_{Met112SO,Met148SO}$) apo A-I (solid bars).

Those of skill in the art are aware of methods and compositions for producing reconstituted lipoproteins (US Pat Appls 20070243136; 20060217312; and 20060205643; U.S. Pat. No. 5,652,339), in general, and as delivery vehicles for imaging agents (US Pat Appl 20070243136 and PCT/US10/52117) and drugs (US Pat Appl 20090110739; U.S. Pat. Nos. 6,306,433, 7,824,709 and 6,514,523), in particular. Such methods include detergent mediated synthesis, co-sonication of HDL components, or through the spontaneous interaction of apolipoproteins with lipids and are described below in more detail. Schematically, the rHDLs and HDL-like compositions of the present invention that contain modified apolipoproteins or fragments thereof are depicted in FIGS. 1, 2A and 2B. As described herein and disclosed in PCT Pat Appl PCT/US10/52117, modification of apolipoproteins does not significantly affect on their ability to interact with lipids and on the structure, stability, and other physico-chemical properties of the formed rHDL particles (FIGS. 6, 7, 8, and 9), and compositions of these particles can be analyzed using the standard methods well-known in the art, including HPLC (FIG. 10). Also, modification does not substantially impair the antiatherogenic ability of rHDL to promote cholesterol efflux (FIG. 11). Thus, the standard methods and compositions well-known in the art can be used to produce, characterize and use the compositions of the present invention.

In preferred embodiments, rHDL-1 are reconstituted HDL particles containing only apo A-$I_{unox}$. In preferred embodiments, rHDL-2 are reconstituted HDL particles containing only apo A-$I_{ox}$. In preferred embodiments, rHDL-3 are reconstituted HDL particles containing apo A-$I_{unox}$ and apo A-$I_{ox}$ with a molar ratio of 1:1. In preferred embodiments, rHDL-4 are reconstituted HDL particles containing apo A-$I_{unox}$, apo A-$I_{ox}$ and apo A-$I_{unox}$ with a molar ratio of 3:3:1.

Figure 3A:
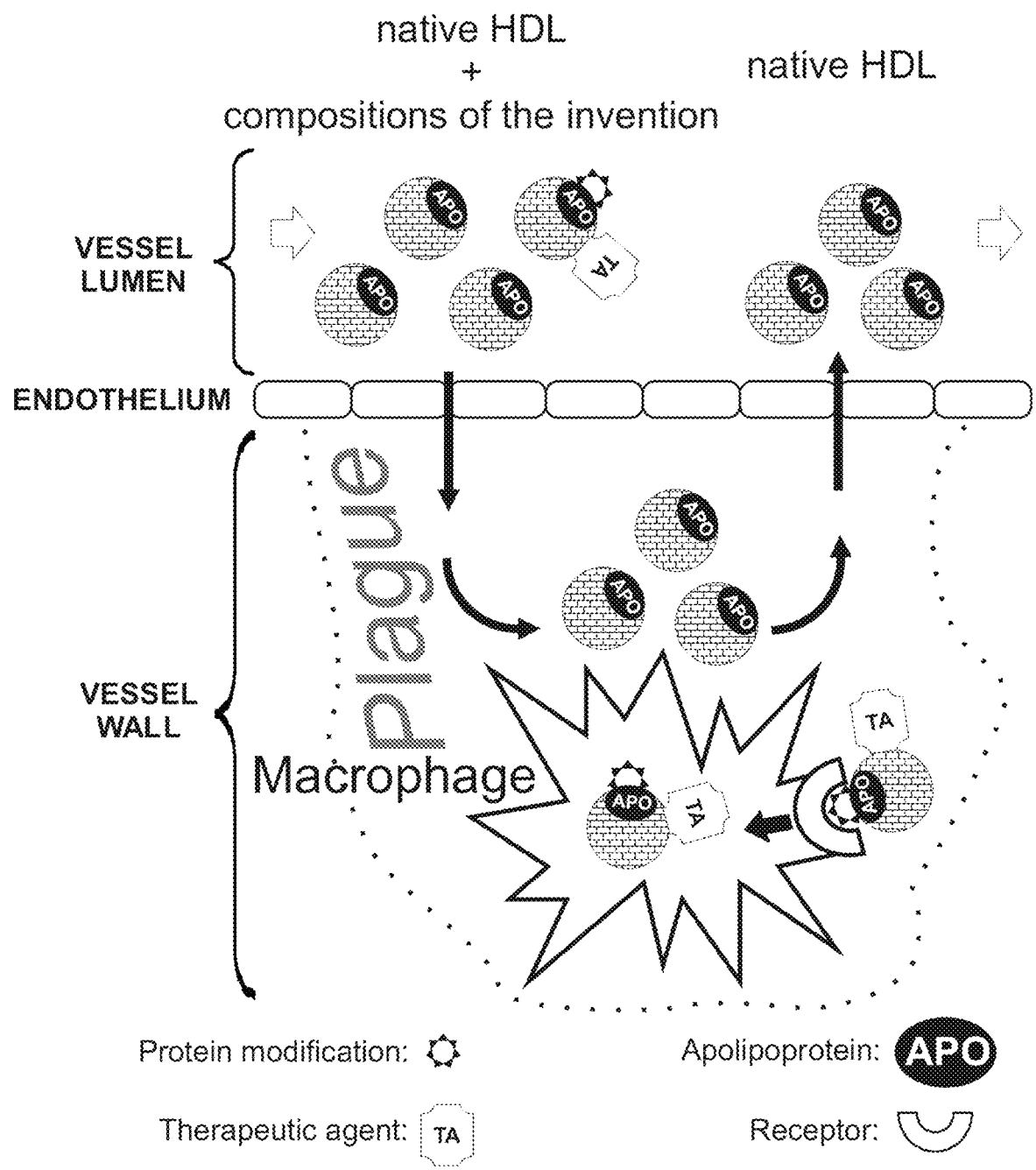
FIG. 3A illustrates a hypothesized molecular mechanism of action of a composition of the present invention with a therapeutic agent attached to said composition as applied to the treatment of atherosclerosis. While not being bound to any particular theory, it is believed that chemical and/or enzymatic modification of protein constituents of high density lipoprotein (HDL) and HDL-like particles of the present invention leads to the recognition of these particles by the macrophage scavenger receptors and results in an irreversible binding to and consequent uptake by macrophages of such particles. It is further believed that accumulation of these particles in the macrophages is accompanied by accumulation of therapeutic agents (TAs) covalently or non-covalently bound to the particles. In contrast, HDL particles that contain only unmodified apolipoprotein molecules are not recognized by macrophages and return to the circulation.
Figure 3B:
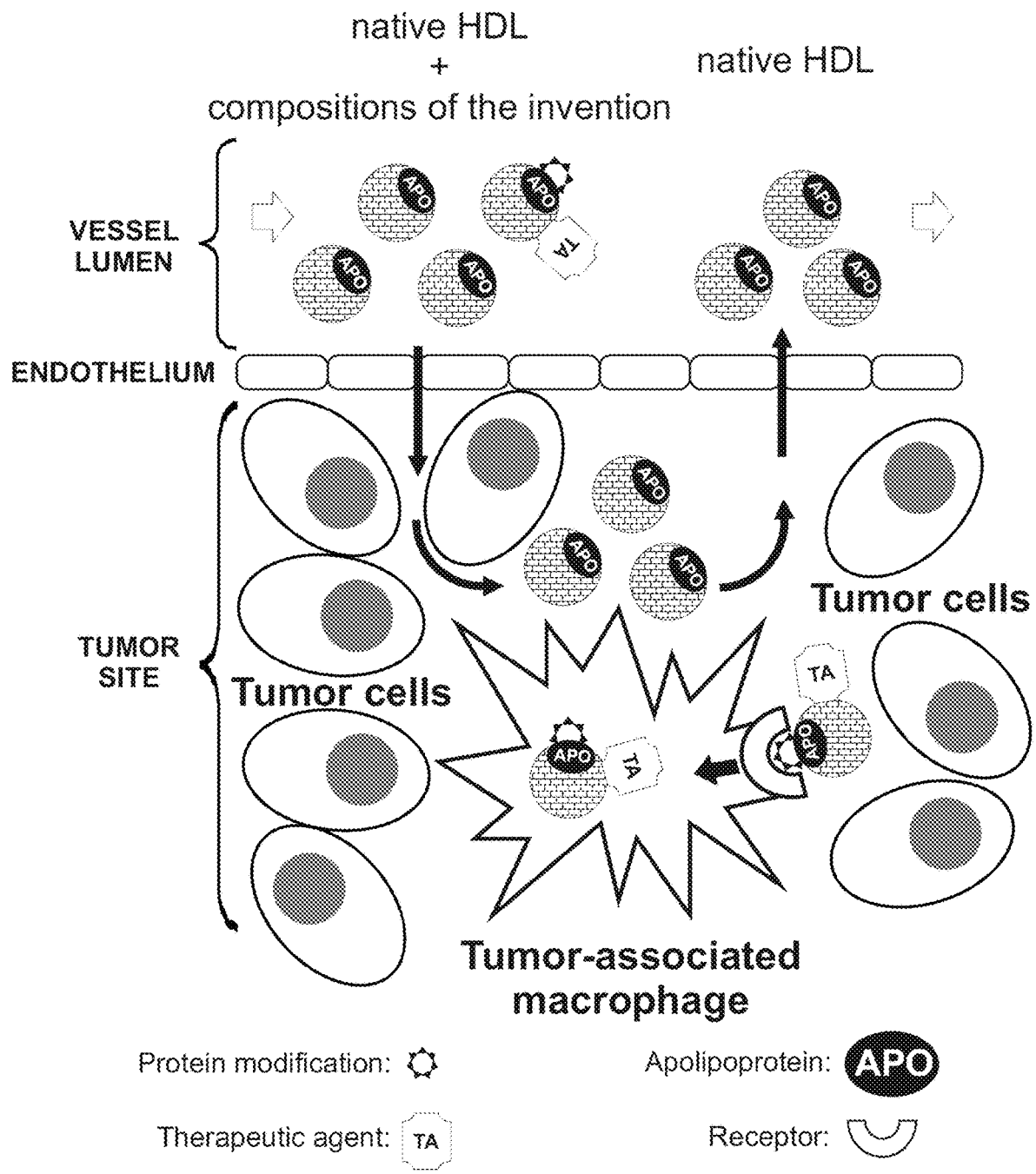
FIG. 3B illustrates a hypothesized molecular mechanism of action of a composition of the present invention with a therapeutic agent attached to said composition as applied to the treatment of cancer. While not being bound to any particular theory, it is believed that chemical and/or enzymatic modification of protein constituents of high density lipoprotein (HDL) and HDL-like particles of the present invention leads to the recognition of these particles by the macrophage scavenger receptors and results in an irreversible binding to and consequent uptake by tumor-associated macrophages of such particles. It is further believed that accumulation of these particles in the macrophages is accompanied by accumulation of therapeutic agents (TAs) covalently or non-covalently bound to the particles. In contrast, HDL particles that contain only unmodified apolipoprotein molecules are not recognized by macrophages and return to the circulation.

The compositions of the present invention have all known advantages of synthetic HDL-based imaging and drug delivery vehicles (US Pat Appls 20070243136 and 20090110739; PCT Pat Appl PCT/US10/52117; U.S. Pat. No. 7,824,709). A distinctive advantage of the methods and compositions of the present invention relative to other lipoprotein-based delivery vehicles known in the art, is that in the particles of the invention, modified apolipoproteins and fragments thereof serve not only as structural proteins that keep stability, integrity and functionality of rHDL and HDL-like compositions but importantly, as specific molecules that target the compositions of the invention to sites of interest. In specific embodiments, modified apolipoproteins and fragments thereof are substrates for macrophage scavenger receptors. In treating cancer, this causes TA-rHDL particles (e.g., paclitaxel-rHDL particles) to be delivered to tumor-associated macrophages and retained in tumor sites (FIG. 3B). Similarly, in preventing and treating atherosclerosis, this causes TA-rHDL particles to be delivered to an atherosclerotic plaque (FIG. 3A). In one embodiment, additional targeting moieties can be used to further facilitate targeting of the compositions of the present invention to a specific site in vivo.

D. Reconstituted Lipoprotein Particles for Targeted Delivery

It is well understood by those of skill in the art that the standard methods well-known in the art can be used to synthesize reconstituted lipoprotein and lipoprotein-like particles that contain imaging agents (US Pat Appl 20070243136 and PCT Pat Appl PCT/US10/52117) or drugs (US Pat Appl 20090110739; U.S. Pat. Nos. 6,306,433, 7,824,709 and 6,514,523; Oda et al. J Lipid Res 2006; 47:260-7; Kim et al. J Hepatol 2009; 50:479-88).

As described in Kim et al. J Hepatol 2009; 50:479-88, and disclosed in PCT Pat Appl PCT/US10/52117, U.S. Pat. Nos. 6,306,433, 7,824,709 and 6,514,523; US Pat Appls 20070243136 and 20090110739, the lipoprotein complexes described herein can be prepared in a variety of forms, including, but not limited to vesicles, liposomes, proteoliposomes, micelles, discoidal and spherical particles.

In preferred embodiments, the rHDL complexes are prepared by the sodium cholate dialysis method with an initial molar ratio of sodium cholate-POPC-cholesterol-apo A-I of 150:80:4:1. This method has been used previously to prepare rHDL with 2 or 3 apo A-I per particle and 9-11 nm diameter.

An aliquot of the resulting reconstituted preparation can be characterized to confirm that the complexes in the preparation have the desired size distribution; e.g., the size distribution of HDL. Characterization of the reconstituted preparation can be performed using any standard method known in the art, including, but not limited to, HPLC (see e.g., FIG. 10), size exclusion chromatography, gel filtration, column filtration, gel permeation chromatography, and non-denaturating gel electrophoresis.

In one embodiment, macrophage scavenger receptors can be used in a functional assay to identify which complex is the most effective in being absorbed and/or uptaken by macrophages. In one assay, the complexes can be tested for their ability to bind macrophage scavenger receptors. Such an assay can differentiate macrophage scavenger receptor-dependent on independent binding to and/or uptake by macrophages. Standard assays that are well known in the art can be used herein to assess binding, uptake and degradation of the compositions of the present invention by macrophages.

The preferred particles of the invention comprise at least one modified apolipoprotein or peptide fragments thereof, at least one amphipathic lipid, and at least one drug attached to these particles by a means selected from the group consisting of adsorption, incorporation, covalent bonding, chelating, and encapsulation.

In one embodiment, the TA comprises the chemotherapeutic agent useful for treating cancer may preferably be selected from the group consisting of doxorubicin (DOX), doxorubicin derivatives (e.g., epirubicin, idarubicin and zyn-linked doxorubicin), paclitaxel (PTX, Taxol®), Taxotere®, campotechin, cisplatin, and the like, as well as of combinations of these agents. In other embodiments, TAs that can be incorporated into the compositions of the present inventions include, but are not limited to, antibiotic agents (bleomycin, mitomycin, amphotericin B, plicamycin, and the like, as well as combinations of these agents), alkylating agents (busulfan, carmustin, lomustine, melphatan, chlorambucil, cyclophosphamide, mechlorethamine, semustine, and the like, as well as combinations of these agents), azidothymidine (AZT), antioxidants (e.g. DHLA), anti-metabolic agents (floxuridine, mercaptopurine, fluorouracil, methotrexate, and the like, as well as combinations of these agents), and mitotic inhibitor agents (etoposide, vinblastine, vindesine, and the like, as well as combinations of these agents).

In preferred embodiments, the TA may preferably be selected from the group of therapeutic proteins and peptides that include, but are not limited to, human growth hormone, bovine growth hormone, vascular endothelial growth factor, fibroblast growth factors, bone morphogenic protein, tumor necrosis factors, erythropoietin, thrombopoietin, tissue plasminogen activator, insulin, antibodies, type-1 interferon, luteinizing hormone releasing hormone (LHRH) inhibitor peptides, vasopressins, platelet aggregate inhibitors, calcitonins, somatostatins, etc. These and other therapeutic proteins and peptides including, but not limiting to, those that are disclosed in US Pat Appl 20070172653 and described in Vlieghe et al. Drug Discov Today 2010; 15:40-56, can be used in the present invention. In still preferred embodiments, the therapeutic peptides include, but are not limited to, peptide inhibitors of immune receptors, T cell receptor (TCR) and triggering receptor 1 expressed on myeloid cells (TREM-1) designed using a novel model of transmembrane signaling, the Signaling Chain HOmoOLigomerization (SCHOOL) model, as disclosed in U.S. patent application Ser. No. 12/895,454 and PCT Pat Appl PCT/US10/52566, other SCHOOL peptide inhibitors (see e.g., US Pat Appl 20090075899), and the like, as well as combinations of these peptide inhibitors.

In preferred embodiments, imaging agents are attached to synthetic nanoparticles of the present invention by a means selected from the group consisting of adsorption, incorporation, covalent bonding, chelating, and encapsulation as described in US Pat Appl 20070243136 and PCT Pat Appl PCT/US10/52117.

In one embodiment, the TA is conjugated to a lipid component of the synthetic nanoparticle. Such a lipid component of the synthetic nanoparticle may be selected from the group consisting of a sterol, a phospholipid, a sterol ester, a diacylglycerol and a triacylglycerol. In certain embodiments, the sterol of the compositions of the present invention is cholesterol. In other embodiments, the sterol ester is cholesteryl ester. In still preferred embodiments, the TA is encapsulated into the synthetic lipoprotein-like nanoparticle.

It is contemplated that the TA may alternatively be conjugated to a modified protein component of the synthetic nanoparticle. Such a modified protein may be selected from the group consisting of a modified apo A-I or fragments thereof, a modified A-II or fragments thereof, and any combination of a modified apo A-I and a modified A-II and fragments thereof.

For the compositions of the present invention, it is critical that the synthetic nanoparticle contain at least one modified molecule of apo A-I and/or apo A-II and/or fragments thereof (FIGS. 1, 2A, 2B). In certain embodiments, the compositions of the present inventions may also comprise unmodified apo A-I and/or apo A-II and/or fragments thereof. In other embodiment, the synthetic nanoparticle of the invention may optionally contain other modified and/or unmodified apolipoproteins including, but not limiting to, A-IV, B, C-I, C-II, C-III, and E, and any combination thereof. In some embodiments, the compositions of the present inventions may optionally comprise protein fragments of modified and/or unmodified apolipoproteins including, but not limiting to, A-IV, B, C-I, C-II, C-III, and E, and any combination thereof.

According to the present invention, HDL-like particle is particularly preferred which has a molar ratio of a modified apolipoprotein (selected the group consisting of a modified apo A-I or fragments thereof, a modified A-II or fragments thereof, and any combination of a modified apo A-I and a modified A-II and fragments thereof) and phospholipid in the range of 1:50 to 1:250, particularly about 1:150. Further, rHDL may optionally contain additional lipids such as cholesterol, cholesterol esters, triglycerides and/or sphingolipids, preferably in a molar ratio of up to 1:20, e.g. 1:5 to 1:20 based on the apolipoprotein. Preferred rHDL is disclosed in U.S. Pat. Nos. 6,306,433, 7,662,410; 7,824,709 and 6,514,523; US Pat Appl 20090110739, PCT Pat Appl PCT/US10/52117, and described in Kim et al. J Hepatol 2009; 50:479-88.

In some aspects of the present invention, rHDL may be prepared from a modified apolipoprotein (selected the group consisting of a modified apo A-I or fragments thereof, a modified A-II or fragments thereof, and any combination of a modified apo A-I and a modified A-II and fragments thereof), and soybean-derived PC, mixed in molar ratios of approximately 1:150 apolipoprotein:PC. In preferred embodiments, egg yolk-derived PC can be used to synthesize the TA-containing HDL-like particles of the invention (US Pat Appl 20090110739). In still preferred embodiments, HDL-like particle may comprise 1,2-dioleoyl-3-trimethyl-ammonium-propane (DOTAP) and cholesterol.

In preferred embodiments, the synthetic nanoparticle of the invention comprises a phospholipid: sterol: apolipoprotein ratio of 180:5:3 (mol:mol:mol). In other preferred embodiments, the synthetic nanoparticle of the invention comprises a phospholipid:apolipoprotein ratio of 100:3 (mol:mol). In still preferred embodiments, the synthetic nanoparticle of the invention comprises a phospholipid: steryl ester:sterol:triglycerides (TG):apo A-I ratio (w/w) of 100:62:25:11:2. In other preferred embodiments, the synthetic nanoparticle comprises a DOTAP:cholesterol ratio of 1:1 (mol:mol) and a lipid/apo A-I protein ratio of 10:1 (w/w). In still other preferred embodiments, the particle of the invention comprises phospholipid bilayers of phosphatidylcholines (PC) and/or phosphatidylglycerol (PG) synthesized as disclosed in U.S. Pat. No. 7,824,709.

The compositions of the invention may comprise between about 80 and about 180 phospholipids per synthetic nanoparticle. Other embodiments define the composition as comprising 2, 3 or 4 apolipoprotein molecules and/or fragments thereof per synthetic nanoparticle. In still further embodiments, the synthetic nanoparticle comprises 1 apolipoprotein molecule and/or fragments thereof to between about 30 and about 60 phospholipid molecules.

The compositions of the invention may further comprise an additional moiety to further facilitate targeting of the agent to a specific site in vivo. The additional targeting moiety may be any moiety that is conventionally used to target an agent to a given in vivo site and may include but is not limited to, an antibody, a receptor, a ligand, a peptidomimetic agent, an aptamer, a polysaccharide, a drug and a product of phage display. In particular embodiments, the targeting moiety may be conjugated to a detectable label. For example, apo E-derived lipopeptide, an apo A-I mimetic peptide, murine (MDA2 and E06) or human (IK17) antibodies that bind unique oxidation-specific epitopes, and gold particles may be used in the present invention to further improve specific targeting macrophages and decrease the required dosage of administered TAs.

Preferably, the diameter or the longest dimension of the nanoparticle is between about 5 nm to about 18 nm. The diameter may be between about 5 to about 12 nm. In particularly preferred embodiments, the diameter is less than 10 nm. In some embodiments the diameter is more than 100 nm.

The composition of the invention may be one which comprises two or more different TAs. In additional embodiments, the composition may further comprise the imaging agents to be delivered together with a TA to sites of interest in vivo and in vitro. In one embodiment, these imaging agents may be selected from the metallic and non-metallic contrast agents disclosed in US Pat Appl 20070243136 and PCT Pat Appl PCT/US10/52117 as well as from any combinations of the imaging and therapeutic agents.

The present invention provides rHDL compositions and HDL-like compositions. These particles can be discoidal and spherical in shape. The compositions of the present invention all contain modified apolipoproteins or fragments thereof (FIGS. 1, 2A, 2B). The particles of the invention are used for targeted delivery of TAs to sites of interest in vivo and in vitro. The TAs are attached to synthetic nanoparticles of the present invention by a means selected from the group consisting of adsorption, incorporation, covalent bonding, chelating, and encapsulation.

Thus, the compositions of the present invention comprise a TA-containing synthetic HDL moiety, the major protein structural components of which, apolipoproteins, or fragments thereof are modified in a means for converting them into specific moieties (for example, into substrates for macrophages) for targeted delivery of HDL-associated TAs to sites of interest (for example, atherosclerotic plaques or tumor sites). The use of synthetic HDL particles that contain modified apolipoproteins or fragments thereof for the targeted drug delivery in vivo is advantageous because after administration, most of these particles get bound and/or uptaken by cells at sites of interest (FIGS. 3A and 3B). This allows a significant reduction in the TA dosage required and thereby limits concerns related to systemic toxicity, which is especially important for chemotherapeutic anticancer agents.

Native HDL particles that contain unmodified lipids and apolipoproteins are not recognized by macrophage scavenger receptors. As a result, native HDL do not irreversibly bind to macrophages and are not uptaken by macrophages. In contrast, modified (for example, oxidized) HDL are readily absorbed by macrophages resulting to accumulation of the modified HDL and their components in macrophage-rich sites such as an atherosclerotic plaque and tumor sites. As described herein, it is unexpectedly found that oxidative modification of only protein constituents or peptide fragments thereof of rHDL is sufficient to convert these particles to substrates for macrophage scavenger receptors and to result therefore in the improvement of association of the TA-(HDL/modified apolipoprotein)-particle with macrophages and/or absorption (uptake) of TA-(HDL/modified apolipoprotein)-particle by macrophages when compared to that of the TA-(HDL/apolipoprotein)-particle constructed with naturally occurring unmodified apo A-I, apo A-II or fragments thereof. Compositions of the invention contain certain chemical or enzymatic modification of apolipoproteins (apo) A-I or A-II or fragments thereof and can be easily and reproducibly produced. The preferred modifications of the apolipoprotein components of the compositions of the invention are those that occur in vivo (e.g., methionine sulfoxidation).

The preferred particles of the invention comprise at least one modified apo A-I and/or A-II or peptide fragments thereof and at least one amphipathic lipid, to form a structure that can be spherical or discoidal. To readily penetrate into the interstitial fluid, the particles must be 25 nm or less in diameter, if spherical, or 25 nm or less in their longest dimension, if discoidal. For structural stability, ease of manufacture, and ability to carry significant amounts of contrast and/or targeting agents, the particles should be at least 5 nm in their largest dimension.

In particularly preferred aspects of the invention the synthetic HDL are reconstituted with the therapeutic agent, modified apolipoproteins and/or fragments thereof, and a second agent that allows the additional targeting of the composition to a specific site. While some of the discussion herein focuses on atherosclerotic plaques and tumor sites, it should be understood that other sites in the body also may be targeted with the compositions of the invention.

As described herein it is unexpectedly found that the TA-containing synthetic HDL composition can be specifically targeted to macrophage-rich sites of interest by chemical or enzymatic modification of the major protein constituents of HDL, apo A-I and A-II, or fragments thereof, solving therefore numerous problems which otherwise are associated with high dosages of TA required and low specificity of formulations in macrophage-targeted drug delivery.

It is contemplated that the compositions of the present invention, in addition to comprising a therapeutic agent and/or a metallic or non-metallic contrast agent (PCT Pat Appl PCT/US10/52117), also may comprise a third agent that is being delivered to affect a therapeutic outcome. Any agent can be delivered in this manner and methods of using lipoproteins to deliver drugs are well known to those of skill in the art (see e.g., U.S. Pat. Nos. 6,306,433, 7,824,709 and 6,514,523; US Pat Appl 2009011073). The therapeutic agent that may be used in the compositions of the invention is limited only by the features that it should not destroy the structural integrity of the rHDL or HDL-like particle.

In specific embodiments, the compositions of the present invention may contain naturally occurring DHLA or its precursor, lipoic acid, LA, to deliver these therapeutic agents to sites of interest in vitro and in vivo (e.g., an atherosclerotic plague). DHLA is formed in vivo from LA, which is widely used as a therapeutic agent in a variety of diseases (see e.g., US Pat Appls 20090068264, 20020110604, and 20020177558). Several lines of evidence suggest that the antioxidant properties of LA and more importantly, its reduced form, DHLA, are at least in part responsible for the therapeutic effect.

DHLA is known in the art to serve as a cofactor for peptide methionine sulfoxide reductase (PMSR), the enzyme that reduces sulfoxidized methionines back to their native form. Therefore, it is contemplated, the compositions of the present invention, in addition to comprising a TA and/or imaging agent (PCT Pat Appl PCT/US10/52117), also may comprise DHLA and/or LA that is being delivered to effect a therapeutic outcome (for example, to reduce methionine sulfoxides in human apo A-I and A-II of atherosclerotic plagues back to their native form). In certain embodiments, the modified apolipoproteins of the compositions of the invention are methionine sulfoxide-containing apo A-I, A-II and/or fragments thereof. Incorporation of DHLA and/or LA in these compositions may result in reducing apolipoprotein methionine sulfoxides of the rHDL compositions back to native methionines after delivery of TAs to sites of interest such, for example, as atherosclerotic plagues and tumor sites.

E. Methods of Use

The invention describes approaches for administering a pharmaceutical agent to an individual. The methods of the invention include preparing and administering a delivery particle as described above that includes the synthetic lipoprotein particle and a drug that is attached to said nanoparticle (FIGS. 1, 2A and 2B). Optionally, therapeutically effective amounts of the delivery particles are administered, in a pharmaceutically acceptable formulation.

The route of administration of the drug, attached to the carrier particle, may vary according to the nature of the pharmaceutical agent to be administered or the condition to be treated. For mammals, the administration is generally parenteral. Routes of administration include, but are not limited to intravenous, intramuscular, subcutaneous, transmucosal, and transdermal. Delivery particles may also be formulated for controlled release. The term "controlled release" as used herein refers to release of a drug from the carrier particle so that the blood or tissue levels of the pharmaceutical is maintained within the desired therapeutic range for an extended period (hours or days).

In one embodiment, the invention provides a method for treating cancer in an individual. The method includes administering a therapeutically effective amount of a chemotherapeutic agent attached to the delivery particles as described above (see also FIGS. 1, 2A and 2B) in a pharmaceutically acceptable formulation. In one embodiment, the agent is paclitaxel.

In particular embodiments, the compositions of the present invention comprising therapeutic and imaging agents or combination of these agents may be used to assess the efficacy or dosing of a particular existing drug. For example, in the case of atherosclerosis, the atherosclerotic lesion size or composition may be monitored prior to and after the administration of a given drug treatment to assess whether the treatment is effective at reducing the size or composition of a lesion.

In particularly preferred embodiments, the compositions of the present invention can be used for targeting macrophages in treating macrophage-related diseases (US Pat Appl 20010002251 and U.S. Pat. No. 7,740,854) including, but not limiting to, the cancers (sarcoma, lymphoma, leukemia, carcinoma and melanoma), bacterial infectious diseases, AIDS, cardiovascular diseases (e.g., arteriosclerosis, atherosclerosis, intimal hyperplasia and restenosis) and other macrophage-related disorders including autoimmune diseases (e.g., rheumatoid arthritis, Sjogrens, scleroderma, systemic lupus erythematosus, non-specific vasculitis, Kawasaki's disease, psoriasis, type I diabetes, pemphigus vulgaris), granulomatous diseases (e.g., tuberculosis, sarcoidosis, lymphomatoid granulomatosis, Wegener's granulomatosus), Gaucher's disease, inflammatory diseases (e.g., sepsis, inflammatory lung diseases such as interstitial pneumonitis and asthma, inflammatory bowel disease such as Crohn's disease, and inflammatory arthritis), and in transplant rejection (e.g., in heart/lung transplants). Examples of macrophage-related diseases are also macrophage-related pulmonary diseases such as emphysema (see e.g., US Pat Appl 20050281740).

The individual components of the rHDL compositions of the present invention may be provided in a kit, which kit may further include instructions for formulating and/or using the therapeutic agents of the invention. Such a kit will comprise a first composition comprising a therapeutic agent, a second composition comprising modified apolipoproteins A-I and A-II and/or fragments thereof, and a third composition comprising a free phospholipid. The kit may further comprise a fourth composition comprising a sterol (e.g., cholesterol). The kit may optionally comprise a fifth composition comprising HDL core lipids (e.g., cholesteryl ester, and TG). The kit may still further comprise a sixth composition comprising imaging agents prepared and characterized as disclosed in PCT Pat Appl PCT/US10/52117. The kit also may comprise a device for delivering the composition to a mammal.

EXAMPLES

The following non-limiting Examples are put forth so as to provide those of ordinary skill in the art with illustrative embodiments as to how the compounds, compositions, articles, devices, and/or methods claimed herein are made and evaluated. The Examples are intended to be purely exemplary of the invention and are not intended to limit the scope of what the inventor regard as his invention. Efforts have been made to ensure accuracy with respect to numbers (e.g., amounts, temperature, etc.) but some errors and deviations should be accounted for.

Standard methods of isolation, synthesis, modification, purification, and characterization of the major protein constituents of the synthetic HDL and HDL-like compositions of the present inventions, the unmodified and modified apo A-I and A-II as well as peptide fragments thereof are well-known in the art (see e.g., PCT Pat Appl PCT/US10/52117).

Example 1

Methods of Reconstitution and Characterization of Reconstituted HDL

As described in Oda et al. J Lipid Res 2006; 47:26-7 and disclosed in PCT Pat Appl PCT/US10/52117, U.S. Pat. Nos. 6,306,433, 7,824,709 and 6,514,523; US Pat App 20090110739 and 20070243136, the standard methods well known in the art can be used to reconstitute HDL as spherical or discoidal particles using the purified apo A-I and A-II as well as peptide fragments thereof, lipids and therapeutic and/or imaging agents. The standard procedures of HDL purification and characterization are also well-known in the art. It should be understood by those of ordinary skill in the art that any of the purified unmodified and modified apo A-I and A-II as well as peptide fragments thereof described herein and in PCT Pat Appl PCT/US10/52117 can be used to produce the compositions of the present invention. However, it is critical for the rHDL of the invention that the rHDL prepared should contain at least one modified molecule of apo A-I and/or apo A-II and/or fragments thereof.

In one embodiment, the homogeneous discoidal rHDL with or without naturally occurring oxidized apo A-I containing methionine sulfoxides at positions 112 and 148 as referred to the apo A-I primary sequences can be prepared using the standard sodium cholate dialysis method well known in the art (see e.g., US Pat Appl 20090110739 and PCT Pat Appl PCT/US10/52117). This method allows to prepare rHDL with 2 or 3 apo A-I per particle and 9-11 nm diameter. Reconstituted discoidal HDL can be characterized using the standard methods (see e.g., U.S. Pat. No. 7,824, 709 and PCT Pat Appl PCT/US10/52117). Exemplary FIGS. 6, 7, 8, 10, and 11 show the results of structural, compositional, and functional analysis of such rHDL.

Oxidative damage to apo A-I in the context of rHDL can be reversed by PMSR in the presence of a source of reducing equivalents (see e.g., PCT Pat Appl PCT/US10/52117). In specific embodiments, the rHDL and HDL-like compositions of the present invention that contain apolipoproteins or fragments thereof with sulfoxidized methionine residues may further contain DHLA to reverse this oxidative modification at sites of interest. Although it is not necessary to understand the mechanism of an invention, it is believed that at sites of interest, DHLA serves as a cofactor for PMSR enzyme to reduce methionine sulfoxides back to their native form.

Example 2

Production of Lipoprotein Apolipoprotein A-1 (LpA-I)-Therapeutic Agent Complexes Preparation of Spherical LpA-I-Paclitaxel Complexes As disclosed in US Pat Appl 20090110739, the particles are prepared by a process involving cholate dialysis to produce a spherical structure with the pharmaceutical enclosed in the interior hydrophobic core region. The lipid mixture (egg yolk phosphatidylcholine (PC), cholesterol and cholesteryl oleate in the ratio of 3.8:1:88.5) and 2 mg paclitaxel (PTX) is dried under nitrogen gas to a thin film and dispersed in dimethylsulfoxide and subsequently in 1.4 ml of 10 mM Tris, 0.1 M KCl, 1 mM EDTA, pH 8.0). Then, 140 ul of sodium cholate (100 mg/ml stock in [0.15 M NaCl 0.003 M KCl, 0.15 M potassium phosphate, pH 7.4, designated as PBS, phosphate buffered saline]) is added to produce mixtures with a final PC to cholate molar ratio of ~1:1.6. Apo A-I (12.7 mg/ml) in 0.4 ml of PBS is added to this mixture and the final volume is adjusted to 2 ml with PBS. The lipid/protein/cholate mixture is then incubated for 12 hrs at 4° C., followed by dialysis (2 liter of PBS, for two days) with three buffer changes. Using $^3$H-cholate as a tracer, <2% of the cholate remains in the LpA-I-PTX preparations. Over 60% of the PTX remains associated with the LpA-I delivery particles as a result of this process. In another embodiment, the spherical LpA-I particles are prepared employing other methods well-known in the art and disclosed in U.S. Pat. No. 6,514,523 and PCT Pat Appl PCT/US10/52117. The obtained particles are purified and characterized using density gradient ultracentrifugation, gel exclusion chromatography, ultraviolet/visible absorbance spectroscopy, gradient gel electrophoresis, electron microscopy, and other standard methods well-known in the art and disclosed in U.S. Pat. No. 6,514,523, US Pat Appl 20090110739, and PCT Pat Appl PCT/US10/52117.

Preparation of Discoidal LpA-I-Amphotericin B Complexes

As described in Oda et al. J Lipid Res 2006; 47:260-7 and disclosed in U.S. Pat. No. 7,824,709, 7 mg of dimyristoylphosphatidylcholine (DMPC) and 3 mg of dimyristoylphosphatidylglycerol (DMPG) are dissolved in chloroform-methanol (3:1, v/v) and dried under a stream of nitrogen gas, coating the vessel wall with the phospholipid. The tube is then lyophilized for a minimum of 2 h to remove residual organic solvent. After this, the lipids are dispersed in 1 ml of PBS (20 mM sodium phosphate, pH 7.0, and 150 mM sodium chloride) by vortexing. To the dispersed lipid, 2.5 mg of amphotericin B (AMB) from a stock solution (30 mg/ml in dimethylsulfoxide (DMSO) is added. Subsequently, 4 mg of apo A-I in 2.0 ml of PBS is added, and the solution (3.1 ml final volume) is incubated at 24° C. The addition of apo A-I leads to a time-dependent decrease in sample turbidity, consistent with the formation of discoidal LpA-I-AMB particles. Full sample clarity is achieved by mild bath sonication (30 s to several minutes). The solution is dialyzed overnight against PBS to remove DMSO and filter-sterilized before use. In another embodiment, the discoidal LpA-I particles are prepared, purified, and characterized employing the methods well-known in the art (see e.g., U.S. Pat. No. 6,514,523 and PCT Pat Appl PCT/US10/52117). The obtained particles are purified and characterized using density gradient ultracentrifugation, gel exclusion chromatography, ultraviolet/visible absorbance spectroscopy, gradient gel electrophoresis, electron microscopy, and other standard methods well-known in the art (see e.g., U.S. Pat. Nos. 7,824,709 and 6,514,523, US Pat Appl 20090110739, and PCT Pat Appl PCT/US10/52117).

Preparation of Lipoprotein-Like Liposomes

As well-known in the art and discussed herein and in PCT Pat Appl PCT/US10/52117, U.S. Pat. Nos. 5,676,926; 7,288,266, 7,588,751, 6,248,353, 6,139,819, 5,676,928, and 5,965,542, US Pat Appls 20070065432, 20060204566, 20090012025, 20080286353, 20090311191, and 20090312402, highly efficient charged liposomes can be used as an improved delivery system for therapeutic and contrast agents. Example is PTX which can be encapsulated into cationic liposomes and used to inhibit tumor growth (PCT Pat Appl PCT/US10/52117). As discussed herein and disclosed in PCT Pat Appl PCT/US10/52117 and U.S. Pat. No. 6,248,353, proteins can be easily incorporated into liposomes by incubating the protein solution with the solution of preformed liposomes. To incorporate therapeutic agents including, but not limited to, anticancer, antiviral, autoimmune and antibacterial agents, cardiovascular agents, anti-inflammatory therapeutics, and antioxidants (e.g., LA and DHLA), standard methods described herein and well-known in the art (see e.g., PCT Pat Appl PCT/US10/52117 and U.S. Pat. No. 6,248,353) can be applied by those of ordinary skill in the art of drug delivery and liposome and lipoprotein formulations. These methods comprise attaching the therapeutics to nanoparticle by adsorption, incorporation, covalent bonding, chelating, and encapsulation. The choice of methods for attachment is practiced by those of ordinary skill in the art of drug delivery and formulations.

As disclosed herein and in PCT Pat Appl PCT/US10/52117, modified apo A-I and A-II and fragments thereof can be easily incorporated in the liposome-based therapeutic and/or contrast agent by incubating the protein or peptide solution with the solution of preformed liposomes. The modified apo A-I and A-II and fragments thereof of the present invention facilitate the targeted delivery and retention of the nanoparticles containing the therapeutic agent to macrophage-rich sites of interest, including but not limiting to, tumor sites and atherosclerotic plaques. This provides a way to increase drug concentrations at specific sites where macrophages are abundant that may allow a reduction in the dosage and, as a result, a decrease in systemic toxicity.

The present example describes methods of preparation of lipoprotein-like liposomes to create the nanoparticles for delivery of therapeutic agents. As described in Kim et al. J Hepatol 2009; 50:479-88, 1,2-dioleoyl-3-trimethylammonium-propane (DOTAP)/cholesterol/apo A-I compositions can be prepared and used for incorporation and delivery of therapeutic agents. Cationic liposomes are prepared by mixing DOTAP and cholesterol in a molar ratio of 1:1. To formulate apo A-I-bound liposomes, cationic liposomes are incubated with apo A-I at a lipid/protein ratio of 10:1 (w/w) overnight at 4° C. The incorporation yield of apo A-I into liposomes is examined by labeling of the lipid component with lissamine rhodamine B-diacyl phosphatidylethanolamine (Rho-PE). The labeled self-assembled Rho-PE/DOTAP/cholesterol/apo A-I liposomes are loaded onto a Sepharose CL-4B column, and both fluorescence intensity and protein concentration are measured in each eluted fraction. DOTAP/cholesterol/apo A-I are used for encapsulation of siRNA and intravenously administered in mice with hepatitis C virus to assess antiviral activity as well as the duration of silencing. The results suggest that DOTAP/cholesterol/apo A-I liposome is a highly potential delivery vehicle to transfer therapeutic agents.

Example 3

Use of Spherical LpA-I-Paclitaxel Complexes Cytotoxicity

As disclosed in US Pat Appl 20090110739, the cytotoxic effect of the LpA-I-PTX preparations on cancer cells can be assessed by the methyl thiazol tetrazolium (MTT) assay. Briefly, cells are plated in 96-well plates (5000 cells/well) in their respective media. Next day, the monolayers are washed with PBS (pH 7.4) twice, and then incubated at 37° C. for 24 h with the LpA-I-PTX complexes in serum-free media. The following day, 25 ml of MTT (1 mg/ml) is added to each well and incubated for 3 h at 37° C. Plates are centrifuged at 1200 rpm for 5 min. The medium is removed, the precipitates are dissolved in 200 ml of DMSO and the samples are read at 540 nm in a microtiter plate reader.

Animal Toxicity

As disclosed in US Pat Appl 20090110739, female C57BL6 mice (6-8 weeks, 18-21 g) can be used in toxicity studies of LpA-I-PTX particles. Groups of six mice each receives injections of 1.5 ml of PBS via the intraperitoneal route, containing respective doses of 30 mg/kg and 40 mg/kg of Taxol®, 40 mg/kg and 70 mg/kg of Abraxane® and 85 mg/kg and 100 mg/kg of LpA-I-PTX. The injections are administered on days 1, 2 and 3. A control group is injected with the LpA-I vehicle. The weights and the health of the mice are monitored for 30 days. Weighings are performed once a day for the first 7 days and twice a week for the remaining monitoring period.

Screening for LpA-I-Paclitaxel Incorporation

Cultured cells are incubated with the LpA-I-PTX complex, labeled with $^{14}$C-PTX. Subsequent to the incubation period, cells are trypsinized and the radioactivity of the lysate is determined to measure the extent of incorporation of the PTX into the cells.

Tumor Suppression

As disclosed in US Pat Appl 20090110739, mice (nu/nu strain, from Harlan, 4-5 weeks old and about 18-22 grams) can be used for tumor suppression studies. Group of 5 mice each animal is implanted subcutaneously with cells harvested from tissue culture of MDA-MB-435 breast cancer cells. When tumor grows to approximately 125 mm$^3$ (100-150 mm$^3$), animals are pair-matched by tumor size into treatment and control groups. Either PTX (TAXOL®; 30 mg/kg paclitaxel) or LpA-I-PTX (80 mg/kg paclitaxel) is intravenously administered to the animals via tail vein. Clinical observations, body weights and tumor volume measurements are made twice a week once tumors become measureable. It should be noted that TAXOL® is formulated with a detergent Cremophor that in itself is cytotoxic and is also the source of numerous side effects during chemotherapy. The Cremophor content of TAXOL® is about 80× that of paclitaxel per ml.

Example 4

Use of Discoidal LpA-I-Amphotericin B Complexes

Yeast Growth Inhibition

As disclosed in U.S. Pat. No. 7,824,709, cultures of the yeast Saccharomyces cerevisiae are grown in yeast extract peptone glucose broth medium (YEPD; Teknova, Hollister, Calif.). Twenty microliters of a saturated overnight culture is used to inoculate 5 ml of YEPD in the absence or presence of either AMB or LpA-I-AMB formulation. Cultures are grown for 16 h at 30° C. with rotation, and the extent of culture growth is monitored by measuring sample turbidity at 600 nm.

Pathogenic Fungi Growth Inhibition

As disclosed in U.S. Pat. No. 7,824,709, microtiter broth growth inhibition assays are conducted with three species of pathogenic fungi: Candida albicans [American Type Culture Collection (ATCC) strain 90028], *Aspergillus fumigatus* (ATCC strain 16424), and *Cryptococcus neoformans* (isolate H99, ATCC strain 208821). Fungi are cultured in RPMI 1640 medium buffered with MOPS to pH 7.0. The final inoculum is 1×10$^6$ cells/ml. Experiments are performed in triplicate at 37° C. for 48 h according to established protocols Inhibitory activity is determined from cultures grown with varying amounts of either AMB or LpA-I-AMB formulation ranging from 0.01 to 16 ug/ml.

Erythrocyte Hemolysis

As disclosed in U.S. Pat. No. 7,824,709, whole blood collected from healthy volunteers is centrifuged for 3 min at 1,000 g. The plasma fraction is removed, and the red blood cells (RBCs) are diluted 1:10 in PBS (or 150 mM NaCl, pH 7-7.4). Deionized water is used as a 100% lysis control. Aliquots (25 ul) of diluted RBCs are transferred to 1.5 ml microfuge tubes, and a given amount of either AMB or LpA-I-AMB or buffer is added to a final volume of 500 ul. Reaction tubes are incubated at 37° C. for 1 or 20 h and centrifuged at 1,000 g for 4 min. An aliquot (200 ul) of the supernatant is added to wells of a microtiter plate containing 25 ul of Drabkins reagent, and sample absorbance at 540 nm is measured on a plate reader.

Cell Viability

As disclosed in U.S. Pat. No. 7,824,709, HepG2 (human hepatoma) cells are grown in MEM (Gibco) supplemented with 4 mM L-glutamine, 0.1 mM nonessential amino acids, 1.0 mM sodium pyruvate, and 10% fetal bovine serum. Cells are split twice weekly into fresh medium and maintained at 37° C. in a humidified 5% $CO_2$ atmosphere. For experiments, the cells are seeded on 24-well plates with 2 ml of complete medium, 2×10$^4$ cells per well. The medium is aspirated after 48 h, the cells are washed with MEM containing 4% FBS, and the wells are each given 2 ml of fresh MEM with 4% FBS. Treatment of cells with either AMB or LpA-I-AMB commences 48 h after seeding at concentrations ranging from 0 to 25 ug/ml. Assays are performed in triplicate. After 20 h of culturing in the presence or absence of antibiotic, cell viability is measured spectrophotometrically using the 3-(4,5-dimethylthiazolyl-2)-2,5-diphenyltetrazolium bromide assay as described by the manufacturer (Sigma). Values are expressed as percentages of absorbance of untreated control cells.

In Vivo Toxicity

As disclosed in U.S. Pat. No. 7,824,709, female BALB/c mice (6-8 weeks old) are divided into groups of three mice each and administered 1, 2, 5, 10, and 15 mg/kg either AMB or LpA-I-AMB intraperitoneally (0.1 ml total volume). At 2 and 6 h after injection, and every 24 h thereafter for 7 days, mice are observed for weight loss or abnormalities in appearance and behavior. Blood is drawn 24 h after drug administration, and liver (alanine aminotransferase and aspartate aminotransferase) and kidney (urea and creatinine) function markers are analyzed.

Efficacy

As disclosed in U.S. Pat. No. 7,824,709, female BALB/c mice (6-8 weeks old) are divided into groups of 10 mice each for a dose-response study of either AMB or LpA-I-AMB efficacy. Each group is inoculated with 5×10$^5$ blastospores of *Candida albicans* (ATCC strain 90028). Two hours after inoculation, mice are treated with PBS or 0.25, 0.5, 1.0, 2.5, or 5 mg/kg of either AMB or LpA-I-AMB. Treatment is administered once a day for 5 days. Over the course of the 28 day observation period, mice are examined twice daily for mortality, weight loss, failure to take food or water, and abnormalities in appearance and behavior.

INCORPORATION BY REFERENCE

The references cited herein throughout, to the extent that they provide exemplary procedural or other details supplementary to those set forth herein, are all specifically incorporated herein by reference.

All of the patents and publications cited herein are hereby incorporated by reference. Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List, or in the text itself; and, each of these documents or references ("herein-cited references"), as well as each document or reference cited in each of the herein-cited references (including any manufacturer's specifications, instructions, etc.), is hereby expressly incorporated herein by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising a reconstituted lipoprotein nanoparticle comprising;
   i) a plurality of phospholipids;
   ii) at least one apolipoprotein comprising a modification, wherein said modification comprises one or two sulfoxidized methionine residues and not a modified tyrosine residue; and
   iii) at least one therapeutic agent attached to said nanoparticle.

2. The composition of claim 1, wherein said at least one apolipoprotein further comprises said modification selected from the group consisting of halogenation, hydroxylation, peroxidation, dimerization, sulfoxidation and nitration.

3. The composition of claim 1, wherein said at least one apolipoprotein is selected from the group consisting of an apolipoprotein A-I, an apolipoprotein A-II and an apolipoprotein A-IV.

4. The composition of claim 1, wherein said at least one apolipoprotein is selected from the group consisting of an apolipoprotein C-I, an apolipoprotein C-II and an apolipoprotein C-III.

5. The composition of claim 1, wherein said at least one apolipoprotein is apolipoprotein E.

6. The composition of claim 1, wherein said nanoparticle further comprises a targeting agent selected from the group consisting of an apo E-derived lipopeptide, an apo A-I mimetic peptide, a murine MDA2 antibody, a murine E06 antibody, a human $IK_{17}$ antibody and a gold particle.

7. The composition of claim 1, wherein said at least one apolipoprotein is an amphipathic apolipoprotein.

8. The composition of claim 1, wherein said therapeutic agent is selected from the group consisting of anticancer agents, antibacterial agents, antiviral agents, autoimmune agents, anti-inflammatory agents, cardiovascular agents, antioxidant agents, and therapeutic peptide agents.

9. The composition of claim 1, wherein said therapeutic agent is selected from the group consisting of paclitaxel, valrubiein, doxorubicin, taxotere, campotechin, and etoposide.

10. The composition of claim 1, wherein said plurality of phospholipids further comprise at least one lipid that is selected from the group consisting of a cholesterol, a cholesteryl ester, a glycolipid, a sphingolipid, a cationic lipid, a diacylglycerol, and a triacylglycerol.

11. The composition of claim 1, wherein said plurality or phospholipids are selected from the group consisting of phosphatidylcholine (PC), phosphatidylethanolamine (PE), phosphatidylserine (PS), phosphatidylinositol (Pt), phosphatidylglycerol (PC), cardiolipin (CL), sphingomyelin (SM), and phosphatidic acid (PA).

12. The composition of claim 10, wherein said cationic lipid is 1,2-dioleoyl-3-trimethylammonium-propane (DOTAP).

13. The composition of claim 1, wherein said plurality of phospholipids further comprises polyethylene glycol(PEG) ylated.

14. The composition of claim 1, wherein said nanoparticle has a diameter of less than about 100 nm.

15. The composition of claim 1, wherein said composition is a pharmaceutical composition comprising a pharmaceutically acceptable carrier.

16. The composition of claim 1, wherein said nanoparticle has a diameter ranging between approximately 5-25 nanometers.

17. The composition of claim 1, wherein said plurality of phospholipids further comprise a chelating agent.

18. The composition of claim 1, wherein at least one of said plurality of phospholipids is modified.

19. The composition of claim 1, wherein said modified apoliprotein comprises a secondary structure that is unchanged as compared to an unmodified apolipoprotein.

20. The composition of claim 1, wherein said nanoparticle is discoidal.

21. A composition, comprising a reconstituted lipoprotein nanoparticle comprising,
   i) a triglyceride-cholesterol ester core surrounded by a plurality of phospholipids;
   ii) at least one apolipoprotein comprising a modification, wherein said modification comprises one or two sulfoxidized methionine residues and nota modified tyrosine residue; and
   iii) at least one therapeutic agent attached to said nanoparticle.

22. The composition of claim 21, wherein said at least one apolipoprotein further comprises said modification selected from the group consisting of halogenation, hydroxylation, peroxidation, dimerization, sulfoxidation and nitration.

23. The composition of claim 21, wherein said at least one apolipoprotein is selected from the group consisting of an apolipoprotein A-I, an apolipoprotein A-II and A an apolipoprotein A-IV.

24. The composition of claim 21, wherein said at least one apolipoprotein is selected from the group consisting of an apolipoprotein C-I, an apolipoprotein C-II and an apolipoprotein C-III.

25. The composition of claim 21, wherein said at least one apolipoprotein is apolipoprotein E.

26. The composition of claim 21, wherein said nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle.

27. The composition of claim 21, wherein at least one apolipoprotein is an amphipathic apolipoprotein.

28. The composition of claim 21, wherein said therapeutic agent is selected from the group consisting of anticancer agents, antibacterial agents, antiviral agents, autoimmune agents, anti-inflammatory agents, cardiovascular agents, antioxidant agents, and therapeutic peptide agents.

29. The composition of claim 21, wherein said therapeutic agent is selected from the group consisting of paclitaxel, valrubicin, doxorubicin, taxotere, campotechin, and etoposide.

30. The composition of claim 21, wherein said plurality of phospholipids further comprise at least one lipid that is selected from the group consisting of a cholesterol, a cholesteryl ester, a glycolipid, a sphingolipid, a cationic lipid, a diacylglycerol, and a triacylglycerol.

31. The composition of claim 21, wherein said plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA).

32. The composition of claim 30, wherein said cationic lipid is 1,2-dioleoyl-3-trimethylammonium-propane (DOTAP).

33. The composition of claim 21, wherein said plurality of phospholipids further comprise polyethylene glycol(PEG)ylated.

34. The composition of claim 21, wherein said nanoparticle has a diameter of less than about 100 nm.

35. The composition of claim 21, wherein said nanoparticle is a pharmaceutical composition comprising a pharmaceutically acceptable carrier.

36. The composition of claim 21, wherein said nanoparticle has a diameter ranging between approximately 5-25 nanometers.

37. The composition of claim 21, wherein said plurality of phospholipids further comprise a chelating agent.

38. The composition of claim 21, wherein at least one of said plurality of phospholipids is modified.

39. The composition of claim 38, wherein said modified apolipoprotein comprises a secondary structure that is unchanged as compared to an unmodified apolipoprotein.

40. The composition of claim 21, wherein said nanoparticle is spherical.

* * * * *